(12) United States Patent
Poulsen et al.

(10) Patent No.: US 6,558,728 B1
(45) Date of Patent: May 6, 2003

(54) α-GLUCURONIDASES OF ASPERGILLUS, PRODUCTION THEREOF AND THEIR USES

(75) Inventors: Charlotte Horsmans Poulsen, Langdalsvej (DK); Masoud R. Zargahi, Molsgade (DK); Ronald Peter de Vries, Van Uvenweg (NL); Jacob Visser, Hinkevordseweg (NL)

(73) Assignee: Danisco A/S (DK)

( * ) Notice: Subject to any disclaimer, the term of this patent is extended or adjusted under 35 U.S.C. 154(b) by 0 days.

(21) Appl. No.: 09/180,570

(22) PCT Filed: May 12, 1997

(86) PCT No.: PCT/DK97/00218
§ 371 (c)(1),
(2), (4) Date: Nov. 10, 1998

(87) PCT Pub. No.: WO97/43423
PCT Pub. Date: Nov. 20, 1997

(30) Foreign Application Priority Data

May 10, 1996 (DK) .............................................. 0565/96

(51) Int. Cl.$^7$ .......................... A21D 10/00; A23K 1/00; C12N 9/00; C12N 9/24; C12N 1/20

(52) U.S. Cl. ....................... 426/549; 426/635; 435/183; 435/200; 435/203; 435/208; 435/209; 435/252.3; 435/254.3; 435/320.1

(58) Field of Search ................................ 435/183, 200, 435/203, 208, 209, 252.3, 254.3, 320.1; 424/94.1, 94.61; 426/635, 549

(56) References Cited

U.S. PATENT DOCUMENTS 4,990,343 A * 2/1991 Haarasilta et al. ............ 426/10

FOREIGN PATENT DOCUMENTS

| EP | 0 406 617 A2 | 9/1991 |
|---|---|---|
| WO | 93/11296 | 6/1993 |
| WO | 94/21785 | 9/1994 |

OTHER PUBLICATIONS

Shao, W., Obi, S.K.C., Pulps, J. and Wiegel, J. (1995) Purification and characterization of the alfa–glucuronidase from Thermonaerobacterium sp. Strain JW/SL–YS485, an important enzyme for the utilization of substituted xylans. Appl. Envion. Microbiol. 61, 1077–1081.

Uchida, H., Nanri, T., Kawabata, Y., Kusakabe, I and Murakami, K. (1992b) Purification and characterization of intracellular alfa–glucuronidase from Aspergillus niger 5–16. Biosci. Biotech. Biochem. 56, 1608–1615.

Bio–Rad Bulletin 1177 EG (1984) Automated protein assay.

Bradford, M.M. (1976) A rapid and sensitive method for the quantitation of microgram quantities of protein utilizing the principle of protein–dye binding. Anal. Biochem. 72, 248–254.

Buchert, J., Siika–aho, M. Rättö, M., Viikari, L. and Bailey, M. (1993) Method and enzymatic preparation for the treatment of cellulose pulps. International Patent Application WO 93/11296.

Bussink, H.J.D.: Buxton, F.P.; Visser, J.; Current Genetics 19:467–474 (1991).

Christov, L.P. and Prior, B.A. (1993) Xylan removal from dissolving pulp using enzymes of Aureobasidium pullulans Biotechnology letters, 15, 1269–1274.

Düsterhöft, E.–M. (1992) Charasterisation and enzymic degradation of non–starch polysaccharides in lignecellulosic by–products. PhD thesis, Wageningen Agricultural University, pp. 2–3.

Harmsen, J.A.M.; Kusters–van Someren, M.A.; Visser, J.; Current Genetics 18:161–166 (1990).

Idouraine, A., Hassani, B.Z., Claye, S.S. and Weber, C.W. (1995) In vitro binding capacity of various fiber sources for magnesium, zinc, and copper. J.Agric Food Chem. 43, 1580–1584.

Ishihara, M., Inagaki, S., Hayashi, N. and Shimizu, K. (1990) 4–O–methyl–D–glucuronic acid residue liberating enzyme in the enzymatic hydrolysis of hardwood xylan. Bull. For. & For. Prod. Res. Inst. 359, 141–157.

Kawabata, Y., Ono, K., Gama, Y., Yoshida, S., Kobayashi, H. and Kusakabe, I. (1995) Purification and characterization of œ—glucuronidase from snail acetone power. Biosci. Biotech. Biochem. 59, 1086–1090.

Khandke, K.M., Vithayathil, P.J. and Murthy, S.K. (1989) Purification and characterization of an alfa–D–glucuronidase from a thermophilic fungus, Thermoascus aurantiacus. Arch. Biochem. Biophys. 274, 511–517.

Korte, H.E. (1990) Reinigung und charakterisierung einer alfa–glucuronidase aus Agaricus bioporus (Lge.) Sing. und untersuchungen an substituieten xylooligomeren. PhD thesis, University of Hamburg.

Milner, Y. and Avigad, G. (1967) A copper reagent for the determination of hexuronic acids and certain ketohexoses. Carbohyd Res. 4,359–361.

Nelson, N. (1944) A photometric adaptation of the Somogyi method for the determination of glucose. J. Biol. Chem. 153, 375–380.

Odier, E. and Artaud, I. (1992) Degradation of lignin in Microbial Degradation of Natural Products (Winkelmann, G. ed.), pp. 161–191.

Perrella, F.W. (1988) EZ–FIT: A practical curve–fitting microcomputer program for the analysis of enzyme kinetic data on IBM–PC compatible computers. Anal. Biochem. 174, 437–447.

(List continued on next page.)

Primary Examiner—Rebecca E. Prouty
Assistant Examiner—Manjunath Rao
(74) Attorney, Agent, or Firm—Hunton & Williams

(57) ABSTRACT

Recombinantly produced α-glucuronidases which are useful in food manufacturing and as a feed additive to enhance the utilization of the feed components, and in other industrial applications such as pulp processing are provided. Genes coding for such enzymes can e.g. be isolated from Aspergillus sp. including *A. tubigensis* or *A. niger.*

27 Claims, 18 Drawing Sheets

OTHER PUBLICATIONS

Figure 1:
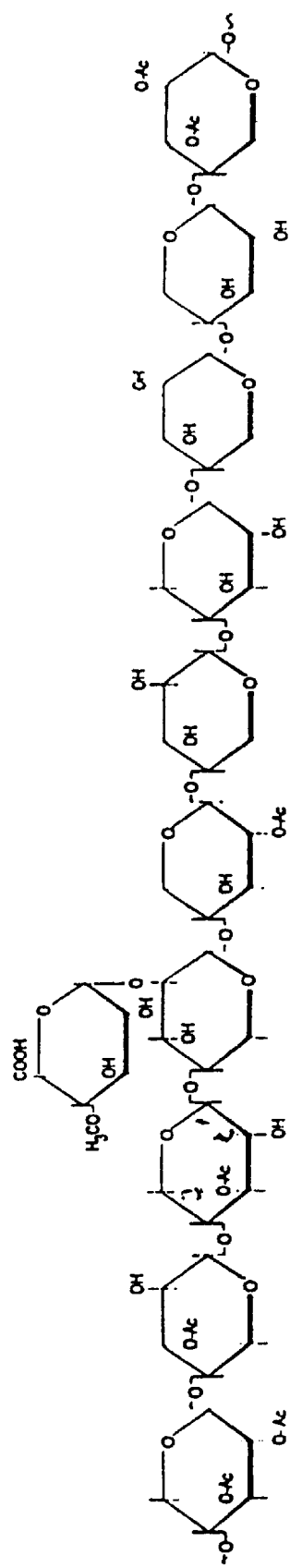

Puls, J. and Schuseil, J. (1993) Chemistry of hemicelluloses: relationship between hemicellulose structure and enzymes required for hydrolysis. In Hemicellulose and hemicellulases (Coughlan, M.P. and Hazlewood, G.P., eds), pp. 1–27. University Press, Cambridge.

Roberts, J.C., McCarthy, A.J., Flynn, N.J. and Broda, P. (1990) Modification of paper properties by the pretreatment of pulp with Saccharomonospora viridis xylanase. Enzyme Microb. Technol. 12, 210–213.

Shao, W., Obi, S.K.C., Pulps, J. and Wiegel, J. (1995) Purification and characterization of the alfa–glucuronidase from Thermonaerobacterium sp. Strain JW/SL–YS485, an important enzyme for the utilization of substituted xylans. Appl. Envion. Microbiol. 61, 1077–1081.

Siika–aho, M., Tenkanen, M., Buchert, J., Puls, J. and Viikari, L. (1994) Anœ–glucuronidase from Trichoderma reesei RUT C–30. Enzyme Microb. Technol. 16, 813–819.

Timell, T.E. (1967) Recent progress in the chemistry of wood hemicelluloses. Wood Sci. Technol. 1, 45–70.

Uchida, H., Kusakabe, I., Kawabata, Y., Ono, T. and Murakami, K. (1992a) Production of xylose from xylan with intracellular enzyme system of Aspergillus niger 5–16. J. Ferment. Bioeng. 74, 153–158.

Uchida, H., Nanri, T., Kawabata, Y., Kusakabe, I and Murakami, K. (1992b) Purification and characterization of intracellular alfa–glucuronidase from Aspergillus niger 5–16. Biosci. Biotech. Biochem. 56, 1608–1615.

Viikari, L. (1994) Use of biotechnology in the pulp and paper industry. Comett course 30.5.–1.6 1994, Finland.

Viikari, L., Kantelinen, A., Sundquist, J. and Linko, M. (1994) Xylanses in bleaching: from an idea to the industry. FEMS Microbiology Reviews, 13, 335–350.

Viikari, L., Tenkanen, M. Buchert, J., Rättö, M., Bailey, M., Siikaaho, M. and Linko, M. (1993) Hemicellulases for industrial applications. In Bioconversion of fresh and agricultural plant residues (Saddler, N., ed), pp. 131–182.

Voragen, A.G.J., Gruppen, H., Verbruggen, M.A. and Viëtor, R.J. (1992) Characterization of cereal arabinoxylans. In Xylans and xylanases (Visser, J. et al. ed.) pp. 51–67.28. Elsevier, Amsterdam.

Welt, T. and Dinus, R.J. (1995) Enzymatic deinking—a review. Progress in Paper Recycling, Feb., 36–47.

Margolles–Clark E. et al.: The alpha–glucoronidase–encoding gene of Trichoderma resei GENE, vol. 172, No. 1, Jun. 12, 1996, pp. 171–172.

\* cited by examiner

```
aatgcgggga gatcctgcaa acaggccatg acgtgtgtat atatgatgaa gaagagggct
ggtactccat agttctttgc gatggcatag ctggaaagaa acggccactA TGAGAGGTTC
AAATCTCTTT CAATTGACCC TGGCTCTTTT ACTGTCCTTG GTAGCAGCCG AGGATGGGTA
CAATGGTTGG CTCCGATATG CTCCCGTGTC CTGCGATCTG CATTGTCGAC AGGCTTTGCC
GTCTCATATT GTGTTGTTGA ACAGCACCAA AGGAAGCCCG ATCGAGACTG CAGGACGAGA
ATTGAAAGCA GGATTCCAAT CGATTCTTTC GACGAACTTA ACATTTCATC CATTTCAATG
CGATAGCTCC GCATCAATTC TGGTGGCTAC CCTGGATGAG TATCGCCAAA AATGCCGGGA
CATCAACTTG CCCGAGCTTG ATCCGATGG CTTCTGGTTA CAATCCGAAG GGGACACAGT
TCGCATCTTA GGCAACAATG CCAGAGGAGC CTTGTACGGA GCATACGAAT ACCTCGCTAT
GGTGGCACAA CGAAACTTCT CTCGTGTCGC GTACACCACC AACCCACATG CGCCGATCCG
TTGGGTAAAT CAATGGGACA ACATGGACGG AAGTATTGAA CGAGGCTACG GTGGCGCGTC
CATATTCTTC AAAGATGGCA CGGTGGTGGA AGACATGGCT CCTGTTGAGC AATATGCTAG
GCTGCTCGCA TCTATACGGA TAAACGCAAT TGTCGTTAAT AATGTCAATG CGAACGCAAC
ACTACTGCTA CCCGAAAATA TGAAAGGCCT GGGTCGCATA GCAGATGCCT GTCGACCATA
CGGCGTTCAA ATTGGCATAT CGCTGAACTT TGCTTCACCA GAAAGCTTGG GCGGCCTAGA
AACTTATGAT CCACTTGATC CTGGTGTCAT TGCATGGTGG CAGAATATCA CCGATAGCCT
CTATACCTAT GTACCAGACA TGGCTGGGTA CCTCGTCAAA GCAGACTCGG AGGGCCAGCC
AGGTCCAGAT ACATATAATC GCACACTCTC ACAAGGGGCG AATCTTTTCG CCCGTGCCCT
GCATCCACAT GGGGGTGTGC TTATGTACCG CGCCTTCGTC TACAACGACA ACTTGAACGA
ATCGGACTGG AAGGCTGATC GTGCCAAGGC AGCAGTGGAA TACTTCAAGG ACCTGGACGG
TCAGTTCTAC GAGAACGTCG TGGTACAGAT AAAGTACGGC CCAATCGACT TTCAAGTACG
CGAGCCTACC TCACCCCTTT TCGCCAACCT CTACCAAACC AACACAGCCA TAGAGTTGGA
GGTTAGTCAG GAGTACCTGG GGCAGCAATG TCATTTGGTG TACCTACCTC CGCTCTGGAA
GACGGTCCTG GATTTTGACT TACGCGTAGA TCACAAGCCT TCGATGGTCC GCGATATAAT
ATCCGGACAG CGCTTCAACA GAACGCTCGG GGGCTGGGCA GCTGTTGTTA ATGTGGGCAC
TAACAGAACA TGGCTGGGTA GCCACCTTGC TATGTCCAAT CTGTACGCTT ATGGTCGTTT
GGCCTGGAGT CCGACAGACG ATTCTGAACA GATCCTCAAA GACTGGACTC GCCTCACATT
TGGACAAAAT CGGCAAGTCA TCGACACTAT TGCTGATATG CCCATGACCT CCTGGCCTGC
CTATGAAAAC TATACAGGCA ACCTGGGCAT ACAGACCCTG ACAGATATCT TGTATACTCA
```

FIG. 10A

```
CTATGGCCCA AACCCAGCTA CACAGGATAA CAATGGCTGG GGTCAATGGA CACGTGCTGA
TCACAATTCA GTTGGAATGG ACCGAACAAT ATCGAATGGC ACTGGGTATA CCGGCCAATA
TCCGGAGGAG GTTGCTCGCT TATACGAGTC ACTAGAAACT ACGCCAGATG ATCTCGTCTT
GTGGTTTCAC CATGTACCAT GGACTCATCG TTTGCATTCC GGGTTGACAG TTATTCAGCA
TTTCTACAAC GCTCACTATG CTGGCTCAGA AGCTGCACAC GGCTTTATAA GACAATGGGA
GTCTTTAAAA GGACTAATTG ATCGGGAGCG ATACGAGGCC ATGCGGTCAC GCCTTGTCTA
CCAGGCGGGA CACTCCATTG TCTGGCGCGA TGCTATCAAC AATTTCTACT ACAACATGAC
CGGAATTCCA GATGTGGCTG GCCGTGTGGG TCATCATCCG TGGCGCATTG AAGCTGAGAG
TATGAGATTG GACGGATACC AGACGTACAC TGTCAGTCCG TTCGAGGCCG CTTCTAACAC
TACGGCAATT ATTACCACCT CTAATTCAAC GACTGGGACA GCAAGAACTA CCATCAAAGC
CCCTTCGGGA GTATATGATA TAGGGGTGAA CTACTACGAT CTCTATGGCG GTCAATCCAA
GTGGACATTA TCTGTGGGTG ACAAGGTAGT GGGTCAATGG CTTGGGGATA TGGAGCATCA
ATCCCTAGGC CATACACCGT CTATATACTT GGACGGTCAC TCGGCCACCC GGATAACGTT
TCATGGGGTC GTCGTCCGGC AGGGTGATCA GCTGAAAATT GTTGGCGAGG CGAATGGGGT
CGAGCCTGCT CCAGTGGATT ATGTAGTGCT GCTACCGCCA GGGGTGGTtg actgatatct
acaaggtcct atgcgctatg taattgccga atatatatgc agatgaaact tttagtggcg
ttctatatca ttggcgttcc agacaaga
```

FIG. 10B

α-GLUCURONIDASES OF ASPERGILLUS, PRODUCTION THEREOF AND THEIR USES

FIELD OF INVENTION

The present invention relates to the provision of α-glucuronidase in pure, isolated form or as a recombinantly produced enzyme and the use;hereof as a xylan side-group hydrolysing enzyme, in particular in food manufacturing, as a feed additive or in processing of cellulosic pulps.

TECHNICAL BACKGROUND AND PRIOR ART

Biodegradation of hemicellulose requires accessory enzyme activities that remove non-xylose substituents, in particular glucuronic acid substituents, from the xylan backbone in addition to endoxylanases and β-xylosidases. The content of glucuronic acid substituents present in xylans varies with the sources of xylan such as hardwood xylans, softwood xylans and cereal xylans.

The configuration of hardwood xylan is presented in FIG. 1. The backbone of hardwood xylan consists of (1,4)-β-D-linked xylopyranose residues. About every tenth xylose unit carries a single, terminal side chain consisting of 4-O-methylglucuronic acid attached directly to the 2-position of xylose. Seven out of 10 xylose residues contain an O-acetyl group at C-2, at C-3, or at both positions (Timell, 1967). Additionally, hardwood xylans contain minor amounts of rhamnose and galacturonic acid residues (Puls and Schuseil, 1993). O-acetyl-4-O-methyl-glucurono-xylan comprise between 10–35% of hardwoods (Timell, 1967).

Softwood xylans consist of a backbone of β-1,4-linked D-xylopyranose residues. There is one 4-O-methylglucuronosyl residue attached to C-2 per 5–6 xylose units. Instead of acetyl-substituents as found in hardwoods, softwood xylans contain alfa-L-arabinofuranose residues directly linked to C-3 of the xylose. One, arabi-nose occurs per eight or nine xylose units, see FIG. 2 (Timell, 1967). Arabino-4-O-methyl-glucuronoxylan amounts to 10–15% of the softwood hemicelluloses (Puls and Schuseil, 1993; Timell, 1967).

Figure 3:
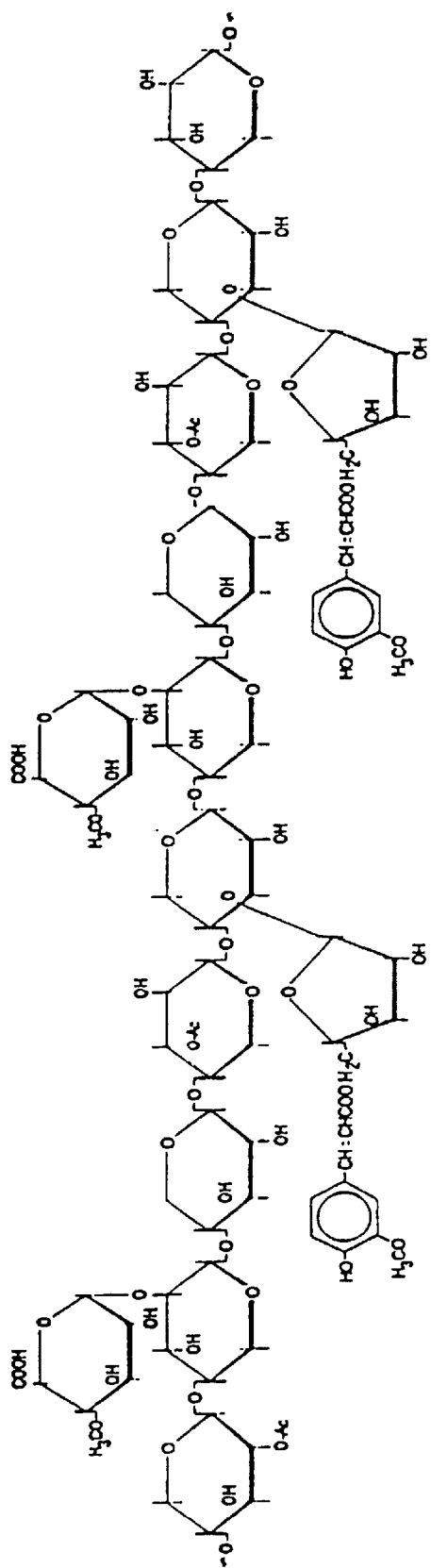

Cereal xylans, which are commonly referred to as arabinoxylans consist of a linear backbone of (1,4)-β-D-linked xylopyranose units to which alfa-L-arabinofuranosyl substituents are attached at O-2 or O-3 or at both of these positions, FIG. 3 (Voragen et al., 1992). There are two main types of arabinoxylans in annual plants. In the endosperms there is a highly branched form which basically is devoid of glucuronic acid. In the more lignified tissues, much less branched forms substituted with additional glucuronic acid residues and/or 4-O-methylether thereof as well as galactose units are found. Glucuronic acid residues are linked to O-2 on the xylan backbone (Viikari et al., 1993)

The amount of glucuronic acid in arabinoxylan varies considerably between cereals of different origins and between fractions of individual cereals. Glucuronoarabinoxylans are found in rice and sorghum and in the bran fraction of wheat, rye and barley and in a number of lignocellulosic by-products like e.g. sunflower meal. There are alsoacetyl groups present in cereal arabinoxylans, particularly in sorghum. They are ester-linked to O-2, O-3 or O-2,3 of xylose. In addition, phenolic acids like ferulic and coumaric acid have been found ester bound to the arabinofuranosyl residues of arabinoxylans (Voragen et al., 1992).

There is currently a considerable industrial interest in the enzymatic hydrolysis of xylans either with the aims of having complete hydrolysis to obtain xylose or with the objective of obtaining enzymatic pulping and bleaching in paper manufacturing.

α-Glucuronidases are produced naturally by several micro-organisms, and up till now isolation of the enzyme from 7 different sources has been described. These source organisms are: *Trichoderma reesei* Rut C-30 (Siika-aho et al., 1994), *Trichoderma viride* (Ishihara et al., 1990), *Aspergillus niger* (Uchida et al., 1992b), *Thermoascus aurantiacus* (Khandke et al., 1989), *Agaricus bisporus* (Korte, 1990), Thermoanaerobacterium sp. strain JW/SL-YS485 (Shao et al., 1995) and *Helix pomatia* (snail) (Kawabata et al., 1995).

The α-glucuronidases isolated from *A.niger* and *Helix pomatia* are intracellular enzymes whereas the others are extracellular enzymes. A molecular weight above 90 kDa are common for these isolated α-glucuronidases. They all have an acidic isoelectric point and pH optimum. The fungal α-glucuronidases, except the Agaricus enzyme are single polypeptide chains, while the bacterial α-glucuronidase, the Agaricus and the snail enzyme are dimers. Isoenzymes have only been found in *Aspergillus niger* (Uchida et al., 1992b).

In general, the specific activity of α-glucuronidase decreases with increasing chain length of the substrate. Only the *Thermoascus aurantiacus* enzyme has any activity on polymeric xylan. The α-glucuronidase from *Helix pomatia* is the only isolated enzyme which had activity towards p-nitro-phenyl-α-D-glucuronide.

Several reports have shown a synergistic effect between xylanase, β-xylosidase and α-glucuronidase in the breakdown of glucuronoarabinoxylans (Siika-aho et al., 1994). α-Glucuronidase therefore has potential application in the total hydrolysis of hemicellulose to produce xylose (Uchida et al., 1992a).

In WO 93/11296 is disclosed a method for the enzymatic treatment of cellulosic pulps where an α-glucuronidase preparation is used to remove metal ions (bound through the carboxylic groups) from the pulp. This improves the bleaching properties of the pulp. Through removal of the glucuronic acid groups the pulp is also-rendered more susceptible to xylanase treatment.

WO 94/21785 discloses xylanases which are useful in food production and which may enhance the utilization of animal feed. However, there is no specific teaching of the use of an α-glucuronidase for such purposes.

Thus, the prior art is silent with respect to improvements which can be obtained specifically by use of α-glucuronidases in the manufacturing of food products including bakery products, and as an additive to enhance the utilization and digestibility of animal feeds. However, as it is described herein, a highly advantageous effect of α-glucuronidase was demonstrated in animal feed ingredients with respect to improving the nutritional value of animal feedstuffs e.g containing annual plants which will result in an enhanced utilization of feed and accordingly of conversion rate for such feedstuffs. Furthermore, nutritionally and quality improving effects of α-glucuronidase alone or in combination with other enzyme activities in dietary fiber-containing food products, such as doughs and finished bakery products including in particular bakery products based on wholemeal, were demonstrated.

Whereas enzyme preparations having α-glucuronidase activity presently can be obtained from microorganisms, in particular fungal species, which produce the enzyme naturally, such preparations are crude in the sense that they contain several other enzyme activities such as cellulase or protease activity. Such impure enzyme preparations are industrially less feasible, since the associated non-α-glucuronidase enzyme activities may be undesirable in several application areas and since it is difficult or impossible to provide enzyme products having a well-defined and standardized α-glucuronidase activity.

Evidently, enzyme preparations only having, or substantially only having α-glucuronidase activity may be provided by extensive purification from media in which α-glucuronidase producing organisms have been cultivated (when the enzyme is secreted out of the cell) or by isolating the enzyme from cells producing the enzyme naturally (when the enzyme is accumulated intracellularly). For specific application areas such as in the food industry such purified, naturally produced α-glucuronidase preparations may be useful.

However, the provision of α-glucuronidase in this manner in industrially needed amounts and at a feasible cost level is not possible due to the low amount of the enzyme being produced naturally in the above source organisms.

It is therefore an important aspect of the present invention to provide the means for producing α-glucuronidase using recombinant DNA technology. Not only will it be possible to provide such recombinantly produced enzyme at a lower cost level, but it will also be possible to obtain α-glucuronidase preparations which do not contain other, undesirable enzyme activities.

SUMMARY OF THE INVENTION

Accordingly, the invention relates in a first aspect to an isolated DNA fragment coding for an enzyme having α-glucuronidase activity, wherein the isolated DNA fragment is obtainable from an Aspergillus species and in a further aspect the invention pertains to a recombinant vector into which such a DNA fragment has been inserted and to a host cell transformed with the vector according to invention.

In a still further aspect there is provided a method of producing α-glucuronidase, the method comprising cultivating the above host cell under conditions where the α-glucuronidase is expressed, and harvesting the enzyme from the cells and/or the cultivation medium.

It is also an objective of the invention to provide a method of improving a dough and/or a baked product comprising adding to the dough an amount of α-glucuronidase which increases the specific volume of the baked product as determined by the rape seed displacement method by at least 5% such as at least 10% and a method of enhancing the nutritional value of an animal feed comprising xylans, the method comprising adding to the feed α-glucuronidase in an amount which results in an increase of the amount of dialysable metal ions in the feed of at least 5%.

In other aspects the invention relates to an isolated, substantially pure enzyme having α-glucuronidase activity, characterised in that it in its glycosylated form has a molecular weight which is about 116 kDa, it has its maximum activity at about 60° C., it shows an isoelectric point of about 5.2 and its pH of optimal activity is in the range of 4.5 to 6, preferably about 5, the enzyme comprising at least one of the amino acid sequences:

(i) EDGYDGWLRYAPVHRDLH (SEQ ID NO:1)

(ii) XDGYDGWLRYAPVSCDLHCRQALPSHIV-LLXSTK (SEQ ID NO:2)

(iii) AGFQSILSTXLTSHPFQXDSSASIL-VATLDXYRQK (SEQ ID NO: 3)

(iv) IXGEADGVEPAPVDYVV (SEQ ID NO: 4)

(v) APSGVYDIGVNYYDLYGGQSK (SEQ ID NO: 5)

(vi) YGPIDFQVREPTSPLFANLYQT-NTAIELEVSQEYLGQQCHF (SEQ ID NO:6)

(vii) WTLSVGDK (SEQ ID NO:7)

(viii) TVLDFDLRVDHKPSMVRDIISGQR-FXRTLGGWAAVVNVGTXR (SEQ ID NO:8)

where X can be any amino acid, and to a method of treating a cellulosic pulp which comprises that the pulp is contacted with the above enzyme under conditions where at least part of the glucuronic acid groups of the pulp is removed.

DETAILED DISCLOSURE OF THE INVENTION

α-Glucuronidase is, as it is mentioned above, produced naturally by several microorganisms, in particular by a number of fungal species. Thus, a DNA fragment coding for the enzyme can e.g. be derived from a Trichoderma species such as *T. reesei*, an Aspergillus species including *A. niger, A. tubigensis* (this species is also sometimes referred to as *Aspergillus tubigensis, A. awamori, A. terreus, A. oryzae*, an Thermoascus species, e.g. *T. auranticus* or an Agaricus species such as *A. bisporus*. Other potential fungal sources of DNA sequences coding for α-glucuronidase include a Schizophyllum species, an Aureobasidium species, a Phanerochaete species, a Fusarium species, a Penicillium species, a Curvularia species, a Tyromyces species, a Cryptonectria species and a Myceliophtora species.

α-Glucuronidase encoding DNA fragments may also be derived from certain bacterial species such as a Thermoanaerobacterium species, a Streptomyces species or a Bacillus species. Additionally, α-glucuronidase encoding DNA sequences may be derived from an animal species such as a snail.

Among the above mentioned source organisms *Aspergillus niger* and *Aspergillus tubigensis* are genetically and physiologically very closely related and morphologically indistinguishable species which differ only in very few phenotype traits.

In a specific embodiment, the DNA fragment coding for α-glucuronidase codes for an enzyme comprising at least one of the amino acid sequences:

(i) EDGYDGWLRYAPVHRDLH (SEQ ID NO:1)

(ii) XDGYDGWLRYAPVSCDLHCRQALPSHIV-LLXSTK (SEQ ID NO:2)

(iii) AGFQSILSTXLTSHPFQXDSSASIL-VATLDXYRQK (SEQ ID NO:3)

(iv) IXGEADGVEPAPVDYVV (SEQ ID NO:4)

(v) APSGVYDIGVNYYDLYGGQSK (SEQ ID NO: 5)

(vi) YGPIDFQVREPTSPLFANLYQT-NTAIELEVSQEYLGQQCH (SEQ ID NO:6)

(vii) WTLSVGDK (SEQ ID NO:7)

(viii) TVLDFDLRVDHKPSMVRDIISGQR-FXRTLGGWAAVVNVGTXR (SEQ ID NO:8)

where X can be any amino acid.

An α-glucuronidase which comprises at least one of the specifically mentioned amino acid sequences may be derived as a native enzyme from a natural source for the enzyme. However, such an enzyme may also in accordance with the invention be provided by means of recombinant DNA technology and thus be produced by a recombinant homologous species or a heterologous species. It has been found that the enzyme as produced naturally may be glycosylated. However, it is envisaged that a heterologous α-glucuronidase producing species may produce the enzyme in a non-glycosylated form. It may be advantageous to provide the enzyme in the non-glycosylated form, since, as it is demonstrated herein, such a form may have a higher activity than the natively glycosylated form. A non-glycosylated form may be provided either by selecting a production microorganism which do not glycosylate the enzyme or by subjecting a glycosylated enzyme to a chemical or enzymatic treatment whereby bound sugars are removed.

In accordance with the invention, α-glucuronidase may be provided as an isolated, substantially pure enzyme preparation, although it may also, for certain industrial purposes, be used as a crude preparation such as the cultivation medium in which the α-glucuronidase producing organism has been cultivated. The purification of α-glucuronidase can be carried out according to any known method for protein purification including the methods which are described in the following examples.

The α-glucuronidase according to the invention may advantageously be-provided as a composition comprising the enzyme and at least one further component. In particular it may be useful to incorporate into such a composition at least one further enzyme, the type of which will depend on the intended use of the composition. Thus, additional enzyme components may be selected from an other hemicellulase such as a xylanase or a β-xylosidase, a cellulase, a lipase, a starch degrading enzyme, a protease and an oxidoreductase. In this context, useful starch degrading enzymes include α-1,4 exo-glucanases such as amyloglucosidases or β-amylases, and α-1,6-endoglucanases including pullulanases and isoamylases, and α-amylase. Useful oxidoreductases include hexose oxidase and glucose oxidase.

With respect to combinations of α-glucuronidase and a xylanyase, it was found that the effect of such combinations depend on the type of xylanase. Xylanases have different substrate affinities such that some types have a preference for water insoluble pentosans (WIP) and others for water soluble pentosans (WSP). As it is described in the following, it may for certain applications, such as in doughs for bread products be advantageous to combine the α-glucuronidase with a xylanase having WIP substrate preference, whereas for other applications including the production of dry cereal bakery products such as crackers, crispbread and biscuits a combination with a xylanase having WSP substrate preference may be preferred.

In specific embodiments of the invention the DNA fragment is derived from an Aspergillus species including as examples *Aspergillus niger, Aspergillus tubigensis* and *Aspergillus awamori*. Specifically, the DNA fragment may comprise the coding sequence as shown in FIG. 10 attached hereto ora derivative or a mutant hereof. In the present context, "derivative or mutant" encompasses any modification of the fragment which implies that the coding sequence when expressed codes for an enzyme having α-glucuronidase activity. Thus, the term includes homologous DNA sequences, the term "homologous" being intended to indicate a DNA sequence which hybridizes to the sequence of FIG. 10 under specified conditions such as e.g. the conditions described in the following Example 5 or. by presoaking in 5×SSC and prehybridizing for 1 h at about 40° C. in solution of 5×SSC, 5×Denhardt's solution, 50 mM sodium phosphate, pH 6.8 and 50 µg of denatured sonicated calf thymus DNA, followed by hybridization in the same solution supplemented with 50 µCi 32-P-dCTP labelled probe for 18 h at about 40° C. followed by washing 3 times in 2×SSC, 0.2 SDS, at 40° C. for 30 minutes.

More specifically, the term is intended to refer to a DNA sequence which is at least 70% homologous to the sequence of FIG. 10, such as at least 75%, at least 80%, at least 85%, at least 90% or event at least 95% homologous. The term is intended to include modifications of the above sequence such as nucleotide substitutions which do not give rise to another amino acid sequence of the α-glucuronidase or nucleotide substitutions which give rise to a different amino acid sequence and therefore, possibly, a different protein structure which might give rise to an α-glucuronidase mutant with different properties than the wild-type enzyme. Other examples of possible modifications are insertion of one or more nucleotides into the sequence, addition of one or more nucleotides at either end of the sequence, or deletions of one or more nucleotides at either end or within the sequence.

One specific example of a DNA fragment according to the invention is the fragment contained in lambda phage which is deposited under the accession No. NCIMB 40801.

In accordance with the invention there is in an important aspect hereof provided a method of producing α-glucuronidase using a host cell which its transformed with a recombinant vector into which a DNA fragment comprising a sequence coding for α-glucuronidase is inserted. Such a sequence can be derived from any cell naturally producing α-glucuronidase including the above mentioned source organisms.

In the present context, the term "host cell" is used to designate any cell which is transformable with a gene coding for α-glucuronidase. Thus, a useful transformable cell may be selected from a fungal species, including a yeast cell, a bacterial cell, a plant cell and an animal cell, the term "transformable" being used to describe the ability of a cell to receive DNA by means of any conventional technique whereby a DNA sequence can be inserted into a cell in a manner allowing the gene to be expressed in the cell. Thus "transformation" in this context encompasses introduction of DNA into a cell by conventional transformation methods, insertion by means of transposable elements or recombination. It will be understood that the DNA which is inserted into a cell may in addition to the sequence coding for α-glucuronidase also comprise sequences regulating the expression of the gene including promoter sequences and initiation and stop sequences and sequences coding for a signal peptide. Specifically, the promoter regulating the transcription of the the coding sequence may be a native promoter for the sequence or it can be a promoter not naturally associated with the coding sequence, i.e. a foreign promoter. The promoter sequence may be inserted on replicon carrying the coding sequence or it may be inserted into a different replicon in such a manner that it is operatatively associated wiht the α-glucuronidase encoding sequence. Advantageously, the promoter may be a promoter which is regulatable by substances in the growth medium or by physical conditions such as temperature.

A plant which is transformed with a gene coding for α-glucuronidase is also contemplated.

The coding sequence and regulatory sequences may be inserted into a chromosome of the transformable recipient cell or may be introduced by means of extrachromosomal replicons such as plasmids. The gene may-be under the control of sequences already present in the cell being transformed or sequences which is introduced with the coding sequence.

The choice of host cell to be transformed will depend on the capacity of a given species or strain to express the gene effectively. In particular it may be advantageous to select a cell which excretes the enzyme out of the cell, i.e. produce the enzyme extracellularly. This evidently reduces the downstream processing considerably, since the enzyme may be harvested directly from the cultivation medium. However, it may be required to use a production strain in which all or part of the enzyme is accumulated intracellularly. In this case the harvesting of the enzyme includes steps whereby the enzyme is isolated from the cells.

In accordance with the invention there is also provided a recombinant host cell which is transformed with a gene coding for α-glucuronidase and the host cell is capable of expressing said gene.

In useful embodiments the microorganism which is transformed with a gene coding for α-glucuronidase is a fungal species selected from a yeast species, a Trichoderma species, an Aspergillus species, a Thermoascus species, an Agaricus species or a bacterial species including a Thermoanaerobacterium species.

Many food products comprise vegetable components which has a content of hemicellulose. The hemicellulose forms part of what is generally referred to as dietary fiber or non-starch polysaccharides. Dietary fiber is generally not degraded by the human or animal digestive enzymes, but the fiber may be at least partially degraded by the intestinal microbial flora. It is, based on the known enzymatic activities of α-glucuronidase, contemplated that the nutritional value of food products can be enhanced by the addition of this enzyme to the products or components hereof, or by subjecting dietary fiber-containing food ingredients to a treatment with the enzyme according to the invention. Thus, in the context of food manufacturing the enzyme may be applied in the manufacturing process or as a food additive. A particularly useful aspect of such uses is the ability of α-glucuronidase to release from the hemicellulose component glucuronic acid groups to which are bound metal ions such as alkaline or earth alkaline metals. When bound to hemicellulose such ions are not bioavailable, but when the metal-glucuronic acid groups are released the metals are in a form where they can be absorbed from the intestinal mucosa. It has been found that the addition of α-glucuronidase to food or feed may result in an increase of the content of metal ions in a dialysable form which is at least 5%, such as at least 10%, preferably at least 15% or even at least 20%.

In accordance with the invention there is provided a method of producing a food product comprising adding to a food product mixture an α-glucuronic acid hydrolysing effective amount of the enzyme according to the invention. It will be understood that such a method can be applied to any food product having a content of substrate for the enzyme and in which it is desirable to obtain at least a partial degradation of the hemicellulose to improve the nutritional or sensory quality of the food product or to improve the manufacturing process.

In particular, the above method will be useful in the manufacturing of cereal-based food products having a high content of hemicellulose including as examples breakfast cereals and bakery products such as bread products e.g bakery products based on wholemeal flour. In the manufacturing of a bakery product the enzyme is conveniently added to the dough or to a component of the dough.

As mentioned above, a particularly advantageous effect of adding α-glucuronidase to a dough is that the quality of the finished baked product is enhanced e.g. with respect to bread volume which can be increased by at least 5%, preferably 10%, more preferably by at least 15% such as at least 20% by adding an effective amount of the enzyme. Such an effect can be obtained by the addition of 1–100 units of α-glucuronidase per 1 kg of flour, such as 1–50 units including 10–30 units.

For the above application in food products or in food manufacturing α-glucuronidase may be used as such or in the form of a composition comprising further components which are useful in the particular use. In particular it may be advantageous to use compositions comprising one or more further enzymes which in a particular food product has advantageous effects.

An interesting aspect of the present invention is the use of α-glucuronidase as a means of enhancing the nutritional value of an animal feed such as "by-products" from production of refined products. Thus, large quantities of by-products of plant origin are produced by the agricultural industry e.g. those parts of crops that remain after removal of value giving components. Examples of such by-products include beet pulp, straws, cereal brans or oil seed meals (Düsterhöft, 1993). These residues still contain considerable amounts of energy, but are often rather indigestible for both animals and humans.

Enzymatic treatment of feedstuffs including treatment with α-glucuronidase may improve their nutritional value by different mechanisms: by degradation of cell walls resulting in improved accessibility or release of intracellular nutrients, by direct utilisation of hydrolysis products of polysaccharides, by elimination of anti-nutritional factors, and by affecting physiological effects exerted by non-starch polysaccharides or by their degradation products (Düsterhöft, 1993). α-Glucuronidase can improve the in vitro digestibility of hemicellulose-containing vegetable material e.g. wheat and corn cob flour as it is demonstrated in the following examples. A specific effect obtained by adding α-glucuronidase to animal feed is a reduction in residual dry matter after digestion of the feed with digestive enzymes in the presence of α-glucuronidase. Preferably, such a reduction is at least 10%, more preferably at least 15% or even at least 20%.

The application of α-glucuronidase to improve the nutritional value of feed components can be in the form of a preparation containing only this enzyme, but it may also be applied in the form of a composition according to the invention. Thus, it may be advantageous to combine α-glucuronidase with one or more enzymes which degrade, hemicellulose such as a xylanase and/or β-xylosidase. As it demonstrated in the examples, synergistic effects with respect to degrading hemicellulose can be achieved by such enzyme combinations.

It will be understood that use of α-glucuronidase to enhance the digestibility or nutritional value of feed can be in the feed manufacturing process e.g. by pre-treating one or more components of the feed with the enzyme or with the composition containing the enzyme or, alternatively, the enzyme or the enzyme-containing composition can be incorporated in the feed as an additive which will enhance the utilization of the feed in the digestive tract of the animal including the effect that metal ions bound to glucuronic acid is brought into a dialysable and absorbable form. This latter effect implies that the manure from the animals will have a lower content of metals.

A particular application of α-glucuronidase which is contemplated is the addition of the enzyme to feed crops such as grass or corn which are subjected to an ensiling process. For such an application it may be advantageous to combine the enzyme according to the invention with other silage additives such as other enzymes, or microbial inoculants.

The α-glucuronidase may also be used for degradation of plant material used for other purposes than as a feed component. Thus, it may in certain industries be desirable to use the enzyme as an auxiliary agent in the processing of plant materials e.g. as a means of facilitating purification or extraction of specific components or in order to alter the water binding capacity of a plant material. The use of α-glucuronidase to enhance the degradability in waste water plants is also contemplated.

The invention also relates to a method of treating a cellulosic pulp as it is mentioned above. The objectives of such a treatment may be several such as delignification during the pulping, enzyme aided bleaching, improved drainage of pulp from recycled paper and production of dissolved pulps (for rayon, viscose etc.). The term "dissolving pulp" refers to a product used for manufacturing of rayon, cellophane, carboxymethyl cellulose, plastics, lacquers, and other cellulose derivatives (Christov and Prior, 1993). E.g. in the production of dissolving pulps for viscose rayon manufacturing it is necessary to remove the xylan selectively (Roberts et al. 1990). In this manufacturing a "clean" cellulose fiber is required and to provide such a raw material a hemicellulose-containing starting materials is advantageously treated with the enzyme or the composition according to the present invention.

Use of recycled paper as raw material in paper manufacturing necessitates de-inking of the recycled paper. Accordingly, the α-glucuronidase according to the invention may be used as a de-inking agent

LEGENDS TO FIGURES

Figure 2:
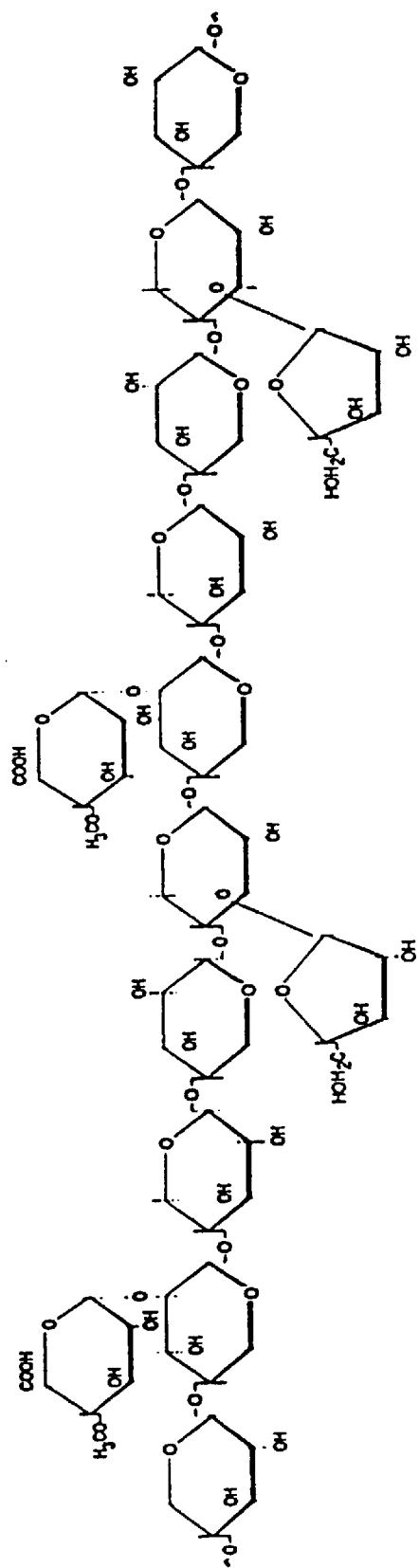
Figure 4:
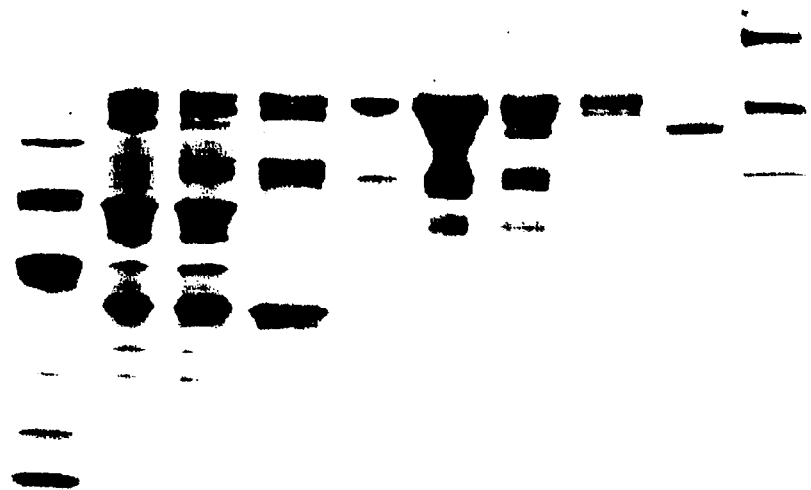
Figure 5:
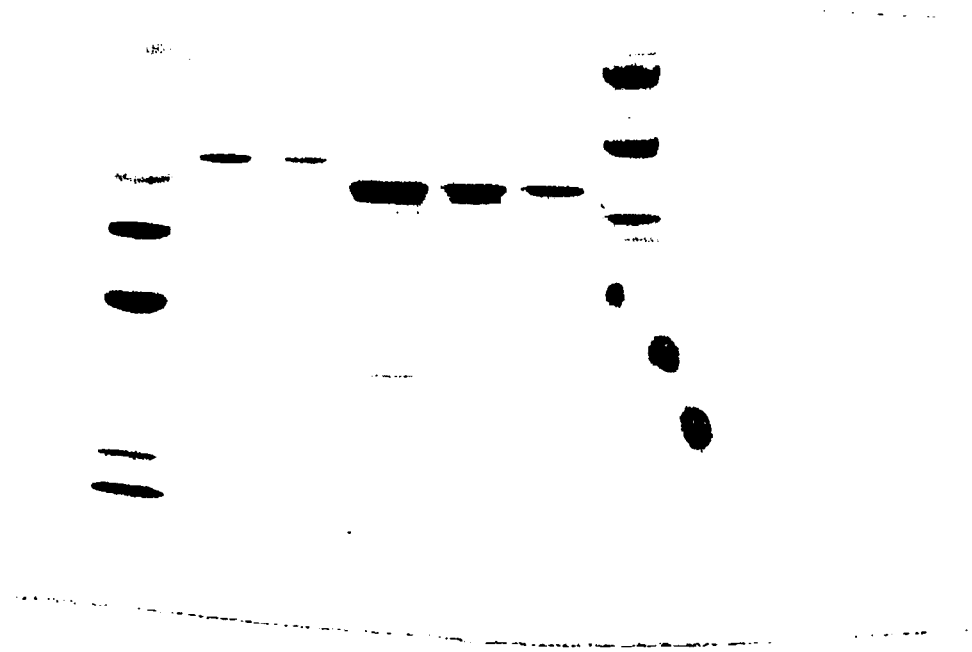
Figure 6:
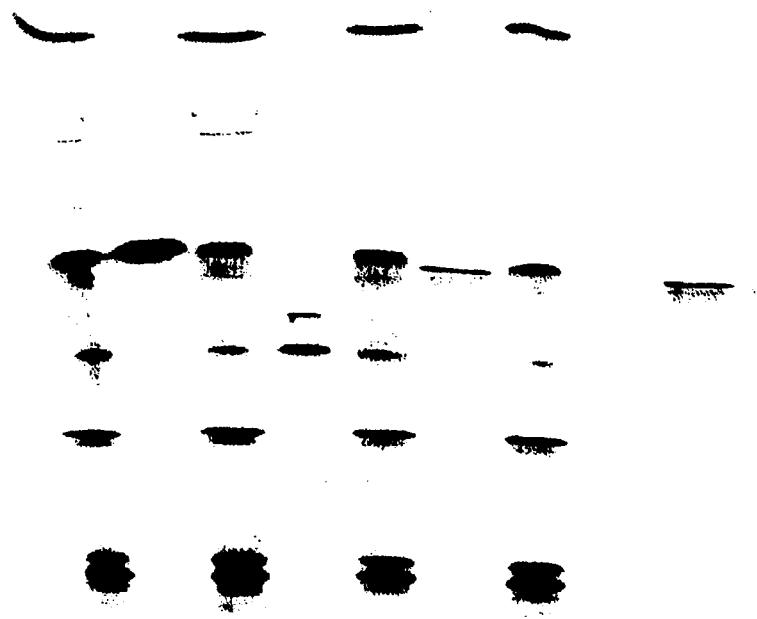
Figure 7:
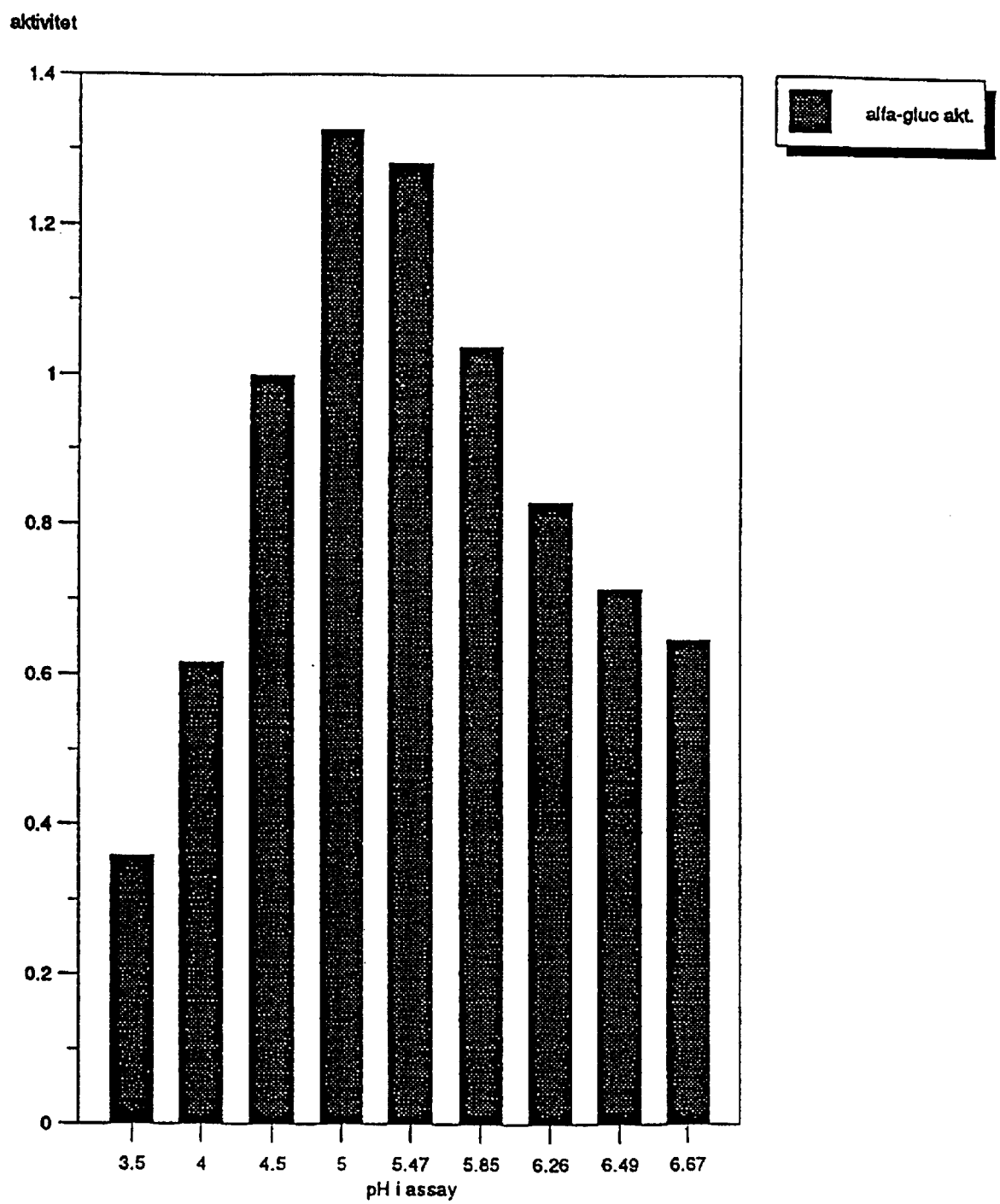
Figure 11:
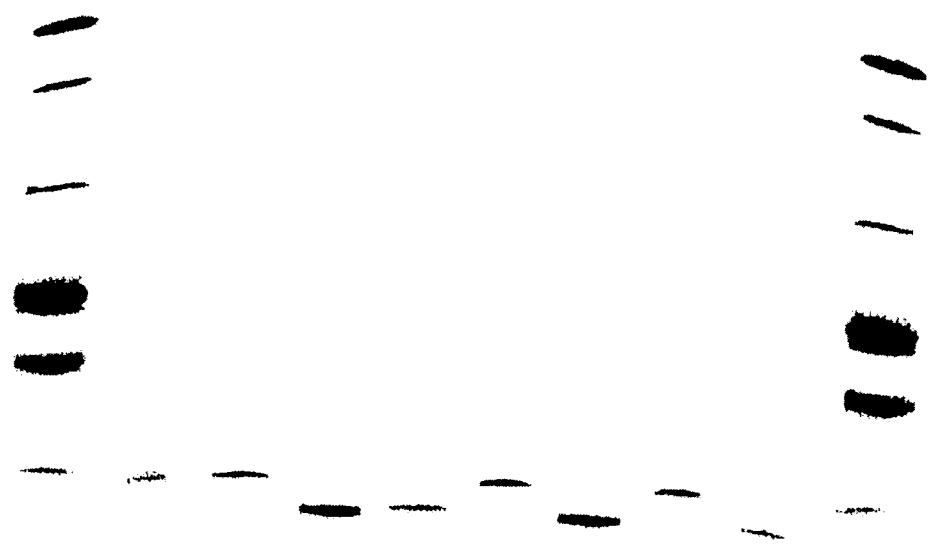
Figure 12:
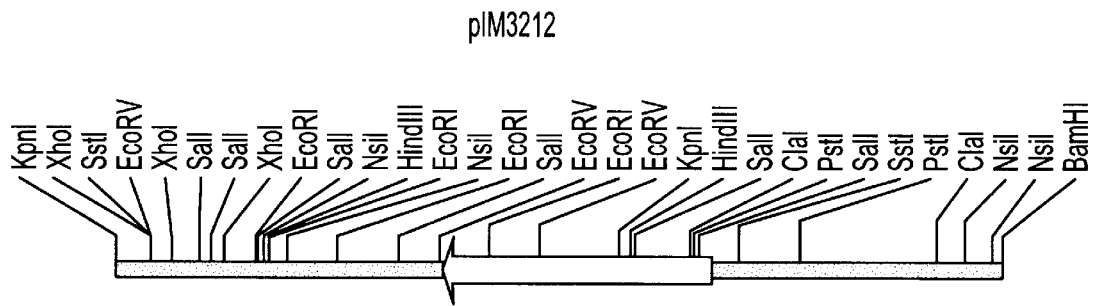

FIG. 1 shows the chemical configuration of hardwood O-acetyl-4-O-methylglucuronoxylan, FIG. 2 shows the chemical configuration of softwood arabino-4-O-methylglucuronoxylan, FIG. 3 shows the chemical configuration of arabinoxylans from grasses, FIG. 4 illustrates SDS-polyacrylamide gel electrophoresis (8–16% Tris-glycine gel) of the different steps in the purification of α-glucuronidase. Lane 1: low molecular weight standard proteins, lane 2: starting material, lane 3: 45% ammonium sulfate precipitate, lane 4: Phenyl Sepharose FF pool, lane 5: Q-Sepharose FF pool, lane 6: Superdex 200 pool, lane 7: Mono Q pool, lane 8: Butyl Sepharose pool, lane 9: Poros Q pool, lane 10: high molecular weight standard, FIG. 5 illustrates SDS-polyacrylamide gel electrophoresis (8–16% Tris-glycine gel) of purified α-glucuronidase before and after deglycosylation with peptide-N-glycosidase F. Lane 1: high molecular weight markers, lane 2, 3 and 4: purified α-glucuronidase after deglycosylation (lane 3 two-fold dilution of lane 4 preparation, lane 2 three-fold dilution), lane 5 and 6: purified α-glucuronidase (lane 5 is two-fold dilution of lane 6), lane 7: low molecular weight markers, FIG. 6 shows isoelectric focusing of purified α-glucuronidase. Lane 1, 3, 5 and 7: isoelectric focusing standard markers pH 2.6 to 6.5, lane 2: β-lactoglobulin A (pI 5.20), lane 4: soybean trypsin inhibitor (pI 4.55), lane 6 and 9: purified α-glucuronidase, lane 8 and 10: empty, FIG. 7 shows pH optimum for purified α-glucuronidase from *Aspergillus niger*, 0.1 M Na—Ac buffers were used, FIGS. 8*a*–*k* summarizes Dionex analysis of degradation products of (4-O-methylglucurono)-D-xylan (birch wood), enzymes were present as indicated in the figures (see materials and methods for experimental details), FIG. 9 is a partial restriction map of DNA region containing the aguA gene. The boxes indicate the fragments used for the cloning the gene and its promoter region, FIG. 10 is a DNA sequence comprising the agua gene from *Aspergillus tubigensis* NW756. The ATG start codon and the stop codon are in bold. The structural gene is in capital letters and the flanking regions are in small letters, FIG. 11 is a SDS-PAGE gel of collected fractions from Poros Q purification of a supernatant of the *Aspergillus niger* transformant NW241::pIM3212.8. Lanes 1 and 10: LMW standards (14,400–94,000 daltons) from Pharmacia; lanes 2 and 6: native α-glucuronidase; lanes 4 and 7: recombinant α-glucuronidase; lanes 5 and 9: deglycosylated recombinant α-glucuronidase, and FIG. 12 is a restriction map of pIM3212.

The invention is further illustrated in the following, non-limiting examples.

EXAMPLE 1

Isolation and Purification of α-glucuronidase from an *Aspergillus niger* Mixed Enzyme Preparation, and Characterization of the Enzyme 1. Materials and Methods 1.1. Chemicals The inorganic chemicals used were of analytical grade. D-glucuronic acid was from Fluka (Buchs, Switzerland). p-Nitro-phenol-β-D-xylopyranoside, xylose and birch wood xylan were from Sigma (St. Louis, U.S.A). Aldotriuronic acid, xylooligosaccharides and Xylazyme tablets were from Megazyme (Warrie-wood, Australia), Endoproteinase Lys-C was from Boehringer-Mannheim (Mannheim, Germany). Peptide-N-Glycosidase F was from Oxford GlycoSystems (Oxon, UK). Q-Sepharose FF, Phenyl Sepharose FF, Superdex 200 PG, Butyl Sepharose FF, molecular weight markers and the FPLC columns Mono Q HR 5/5 and Superose 6 HR 10/30 were purchased from Pharmacia (Uppsala, Sweden). Poros 10 HQ media was from PerSeptive Biosystems, Cambridge, Mass., U.S.A. Sumizyme AC (#1303) was from Sumitomo, Japan. The DIONEX PA 100 column was from DionexCorp., Sunnyvale, Calif., U.S.A.

1.2. α-Glucuronidase Assay

The incubation mixture (total volume 0.2 ml) contained 0.16 ml substrate [2 mg/ml solution of aldotriuronic acid/ aldobiuronic acid (approximately 80:20) (GPA-$X_{1,2}$)]—aldotriuronic acid=2'-O-(4-O-methyl-α-(1-2)-D-glucuronosyl)-β-D-xylopyranosyl-(1-4)-D-xylopyranose (Megazyme)—in 0.05 M Na-acetate (Na—Ac) buffer, pH 5.0 and 0.04 ml of enzyme solution to be assayed. The incubation was started by the addition of enzyme. After incubation for 30 min. at 40° C., the reaction was stopped by boiling the samples for 4 minutes. If there was a precipitate, the sample was centrifuged and transferred to another Eppendorf tube.

To each tube was added 0.6 ml copper reagent prepared according to Milner and Avigad (1967). The assay was boiled 10 min. and then cooled in an ice bath.

Subsequently 0.4 ml arsenbmolybdate reagent prepared according to Nelson (1944) was added and after gentle shaking 0.8 ml $H_2O$ was added. After mixing the assay was measured at 600 nm against $H_2O$.

Blanks were prepared by boiling a complete assay at time zero, before incubation at 40° C. A substrate blank was made by adding water instead of enzyme solution.

A standard curve was prepared using D-glucuronic acid. One α-glucuronidase unit is the amount of enzyme releasing 1 μmol of glucuronic or methylglucuronic acid per min under standard assay conditions.

1.3. β-xylosidase Assay

The assay contained 600 μl of substrate (5.5 mg of p-nitrophenyl-β-D-xylopyranoside in 6 ml 50 mM Na—Ac (pH 4.2) and 100 μl of purified α-glucuronidase. The assay was incubated at 40° C. At time 0, 7, 15 and 22 min, respectively, a 100 μl sample was removed and added to 600 μl of stop reagent (0.13 M $Na_2CO_3$). The absorbance at 405 nm was read. A substrate blank was made by adding water instead of enzyme solution.

One β-xylosidase unit is the amount of enzyme which releases 1 μmol of xylose per minute at 40° C. from 1 mM p-nitrophenyl-β-D-xylopyranoside.

1.4. Xylanase Assay

Xylanase activity was determined as the amount of blue colour released from azurine-dyed cross-linked birch wood xylan (Xylazyme tablets) essentially as described by the manufacturer. Xylanase activity is expressed as GPU units which refers to an internal standard with a given activity.

1.5. Protein Measurement

During the course of α-glucuronidase purification, the protein eluted from the columns was measured by the absorbance at 280 nm. The protein in the pooled samples was determined in microtiter plates by a sensitive Bradford method (Bradford, 1976) according to Bio-Rad (Bio-Rad Bulletin 1177 EG, 1984). Bovine serum albumin was used as a standard.

1.6. Polyacrylamide Gel Electrophoresis (PAGE)

SDS-PAGE, native gel electrophoresis and isoelectric focusing were carried out using a NOVEX system with precast gels. Electrophoresis and silver staining of the gels were done according to the manufacturer's recommendation (Novex, San Diego, US).

1.7. Determination of Molecular Weight

The size of the native α-glucuronidase was determined by gel permeation chromatography on a Superose 6 column at a flow rate of 0.5 ml/min with 20 mM triethanolamine (pH 7.3) as eluent and ribonuclease A (13.7 kDa), ovalbumin (43 kDa), aldolase (158 kDa) and catalase (232 kDa) as size standards.

1.8. Purification of α-glucuronidase

α-Gluculronidase was isolated from a crude, mixed enzyme preparation, Pektinse 146 which is marketed as a pectinase, source (Danisco Ingredients, Brabrand, Denmark), derived from an Aspergillus strain having the reference number 4M146 and presently designated as *Aspergillus niger*. All procedures took place at room temperature.

To 200 ml of Pektinase 146 was added $(NH_4)_2SO_4$ to 45% saturation. After stirring for 30 min the precipitated protein was recovered by centrifugation for 20 min at 11,000 g. The resultant pellets were solubilized in 120 ml Phenyl Sepharose buffer (20 mM sodium acetate (pH 5.0), 1.5 M $(NH_4)_2SO_4$). The resulting solution was applied to a column of 155 ml (5×7.9 cm) Phenyl Sepharose FF equilibrated in Phenyl Sepharose buffer. The column was washed with Phenyl Sepharose buffer. α-Glucuronidase was eluted using a 1320 ml linear gradient from 1.5 M to 0 M of $(NH_4)_2SO_4$ in 20 mM sodium acetate (pH 5.0) at a flow of 4 ml/min. Fractions of 12 ml were collected. Fractions 60–101 (500 ml) were pooled and concentrated and desalted into Q-Sepharose buffer (20 mM triethanolamine, pH 7.3) by ultrafiltration in an Amicon 8400 unit equipped with a 10 kDa membrane. The resulting sample was applied to a 106 ml column (2.6×20 cm) of Q-Sepharose FF equilibrated in Q-Sepharose buffer. After washing with 240 ml of equilibration buffer α-glucuronidase was eluted with a linear salt gradient from 0 to 1 M NaCl in Q-Sepharose buffer. The flow was 3 ml/min and fractions of 7.5 ml were collected.

Fractions 23–36 (105 ml) were pooled and concentrated by ultrafiltration in an Amicon 8400 unit equipped with a 10 kDa cutoff membrane. The concentrate (7 ml) was loaded onto a column of Superdex 200 PG (180ml, 2.6×33 cm) equilibrated in 20 mM sodium acetate (pH 5.0), 0.1 M NaCl. The column was eluted at a flow of 1 ml/min and fractions of 2 ml were collected. α-Glucuronidase eluted in fractions 22–41 which were pooled.

After concentration and desalting as above the pool was separated on a Mono Q HR5/5 column in 6 runs. Mono Q buffer was 20 mM triethanolamine (pH 7.3). The column was eluted with a NaCl gradient in the same buffer. The flow was 1.5 ml/min. Fractions of 0.75 ml were collected. The relevant fractions from each run were pooled, giving a total of 27 ml after 6 runs. To this pool was added $(NH_4)_2SO_4$ to 1.5 M and the sample was applied onto a 30 ml (1.6×15 cm) column of Butyl Sepharose FF using Phenyl Sepharose buffer. After washing with 50 ml of the same buffer α-glucuronidase was eluted with a linear gradient from 1.5 M to 0 M $(NH_4)_2SO_4$ in Phenyl Sepharose buffer at a flow of 2 ml/min. Fractions of 4 ml were collected. Fractions 22–26 were pooled (20 ml).

The pool was concentrated and desalted as above. Final purification was obtained on a 4 ml Poros 10 HQ column (1×5 cm) equilibrated in Q-Sepharose buffer. 5 ml per run (total 3 runs) were loaded on the Poros Q column with a flow of 2 ml/min. Elution was carried out with a linear salt gradient of NaCl in Q-Sepharose buffer. Fractions of 1 ml were collected and screened for α-glucuronidase activity. A summary of the purification is provided in Table 1.1 below.

1.9. Amino Acid Sequencing

The purified freeze-dried enzyme (100 μg) was dissolved in 50 μl of 8 M urea, 0.4 M $NH_4HCO_3$, pH 8.4. After overlay with $N_2$ and addition of 5 μl of 45 mM dithiothreitol, the protein was denatured and reduced for 15 min at 50° C. under $N_2$. After cooling to room temperature, 5 μl of 100 mM iodoacetamide was added for the cysteine residues to be derivatized for 15 min at room temperature in the dark under $N_2$. Subsequently, 135 μl of water and 5 μg of endoproteinase Lys-C in 5 μl of water was added and the digestion was carried out at 37° C. under $N_2$ for 24 hours. The resulting peptides were separated by reverse phase HPLC on a VYDAC C18 column (0.46×15 cm; 10 μm; The Separation Group, Calif., US) using solvent A: 0.1% TFA in water and solvent B: 0.1% TFA in acetonitrile. Selected peptides were re-chromatographed on a Develosil C18 column (0.46×10 cm, Novo Nordisk, Bagsværd, Denmark) using the same solvent system, prior to N-terminal sequencing.

Sequencing was done on an Applied Biosystems 476A sequencer using pulsed-liquid fast cycles according to the manufacturer's instructions (Applied Biosystems, Calif., US). For direct N-terminal sequencing the purified protein was passed through a Brownlee C2 Aquapore column (0.46×3 cm, 7 μm, Applied Biosystems, Calif., US) using the same solvent system as above. N-terminal sequencing was then performed as described above.

1.10. Deglycosylation

Deglycosylation of the pure α-glucuronidase was performed using Peptide-N-Glycosidase F from Oxford GlycoSystems (Oxon, UK) according to the manufacturer's recommendations, with denaturation of the protein before addition of Peptide-N-Glycosidase F.

1.11. Hydrolysis Experiments 1.11.1. α-Glucuronidase activity as a function of addition of xylanase and β-xylosidase.

2.5 ml of a 0.5% solution of birch wood xylan in 50 mM sodium acetate (pH 5.0) was incubated with 0.45 units of purified α-glucuronidase after Poros chromatography, 35 GPU purified xylanase 1 from *Asperqillus niqer*, 29 GPU of xylanase complex (Sumizyme AC, an *Asperqillus niger* product containing 16104 GPU units per g., desaited on a PD-10 column into the incubation buffer), 0.48 units of β-xylosidase (gift from Leo de Graaff, Wageningen), respectively. The 4 enzymes were incubated alone and in all possible combinations in total volumes of 3.25 ml. The samples were incubated for 3 hours at 45° C. Blanks were made by incubation with buffer instead of the enzyme solutions. The incubation was stopped by boiling the samples for 3 min. Free α-glucuronic acid was then determined by the colour reaction as described for the α-glucuronidase assay. The samples were analyzed by anion exchange chromatography on a Dionex hPLC system equipped with a Dionex PA 100 column and a pulsed electrochemical detector with pH reference electrode and range 1 μC. Elution was carried out using a 12 min linear gradient from 0.02 M to 0.05 M, followed by a 33 min linear gradient from 0.05 M to 0.12 M Na-acetate gradient in 0.1 M NaOH at a flow rate of 1 ml/min.

1.11.2. Xylanase activity as a function of α-glucuronidase addition

Xylanase complex (1% Sumizyme AC, an *Asperqillus niger* product containing 16104 GPU units per g., desalted on a PD-10 column into 20 mM Na-acetate, pH 5.0, then diluted 8 times) was assayed for xylanase activity in the presence and absence of purified α-glucuronidase, 0.16 units per incubation. Total incubation volume was 1.7 ml. Incubation temperature was 45° C., time 10 min.

1.12. Temperature Optimum

The enzyme activity was measured as described above with incubation for 10 min in 0.05 M Na-acetate buffer, pH 5.0, at various temperatures.

1.13. pH Optimum

α-Glucuronidase activity was measured as described above. 0.1 M Na-acetate was used in the pH range 3.5 to 6.7, pH values were determined in the assay tube at room temperature.

1.14. Temperature Stability

Eppendorf tubes with 200 μl of purified α-glucuronidase in 50 mM sodium acetate buffer (pH 5.0) were incubated in a water bath at the respective temperatures for 20 hours. Then the α-glucuronidase activity was determined as described above.

1.15. pH Stability

Purified α-glucuronidase (150 μl) was maintained at room temperature in 500 μl of 0.2 M Na-acetate (pH 4.0), 0.2 M bis-tris (pH 6.0) or 0.2 M tris (pH 8.0), respectively for 3, 10, 13, 28 and 62 days, respectively and the residual activity assayed as above.

2. Results 2.1. Purification of α-glucuronidase

α-Glucuronidase was purified as described under Materials and znethods. A summary of a typical purification scheme is shown in Table 1.1. The starting material, Pektinase 146 had an α-glucuronidase activity of 0.14 μmol/min/mg of total protein which was high compared to the values reported in the literature for most other sources of α-glucuronidase.

TABLE 1.1

Summary of α-glucuronidase purification

| Fraction | Protein (mg) | Total activity (μmol/min) | Specific activity (μmol/min per mg prot) | Purification factor | Yield (%) |
|---|---|---|---|---|---|
| Pektinase 146 | 2740 | 380 | 0.14 | 1 | 100 |
| 45% (NH$_4$)$_2$SO$_4$ | 1899 | 300 | 0.16 | 1.1 | 79 |
| Phenyl Sepharose | 619 | 195 | 0.31 | 2.2 | 51 |
| Q-Sepharose | 88 | 162 | 1.83 | 13.1 | 42 |
| Superdex 200 | 57 | 102 | 1.80 | 12.9 | 27 |
| Mono Q | 11 | 69 | 6.20 | 44.3 | 18 |
| Butyl Sepharose | 2.2 | 54 | 24.5 | 175 | 14.2 |
| Poros Q | 0.42 | 22 | 52.3 | 371 | 5.8 |

The ammonium sulfate precipitation applied as the first step did not result in much purification with respect to an increase in specific activity, but this step was important for the later steps in the purification by removing coloured contaminants (phenolic compounds) which otherwise interfered with the column chromatography steps.

Both Phenyl-Sepharose and Q-Sepharose chromatography were highly reproducible steps with a good recovery and purification rate. Gel filtration constantly resulted in loss of activity but this step could not be omitted in the purification procedure.

After gel filtration further purification was obtained by anion exchange on a mono Q column and hydrophobic interaction chromatography on a Butyl-Sepharose column. These two steps were both highly reproducible and gave a good separation with a high recovery.

The essential step was the application of a Poros Q column which had a high selectivity for α-glucuronidase resulting in an appreciable purification even though it was applied at a stage were the enzyme had been through both an Q-Sepharose and a Mono Q anion exchange column. However, the separation capacity of the Poros Q was poor compared to a Mono Q column and it was not possible to eliminate a step and use Poros Q alone instead of the Mono Q column.

Throughout the purification α-glucuronidase always eluted as a single peak. The purified ot-glucuronidase was assayed for β-xylosidase activity on p-nitrophenyl-β-d-xylopyranoside, and had as expected no activity on this substrate. The enzyme was purified about 371-fold, and the yield was 5.8%. A SDS polyacrylamide gel electrophoresis gel showing the different steps of the purification is shown in FIG. 4.

2.2. Molecular Weight

The apparent molecular weight of α-glucuronidase was 107,000 as measured by SDS-PAGE: (FIG. 4). By gel filtration on Superose 6 the molecular weight was determined to 100,000. This indicates that the α-glucuronidase from *Aspergillus niger* is composed of one peptide chain. The two intracellular α-glucuronidases which were isolated from *Aspergillus niger* by Uchida et al. (1992) were both 130,000 by SDS-PAGE and 150,000 by gel filtration. The extracellular enzyme according to the invention therefore seems to be different from those two intracellular enzymes.

2.3. Deglycosylation

The result of deglycosylating the purified α-glucuronidase is shown in FIG. 5. The enzyme was incubated in denatured state with peptide-N-Glycosidase F. This enzyme is highly specific, cleaving only the β-aspartylglycosylamine bond between asparagine and the innermost N-acetylglucosamine of the glycan. As a consequence the asparagine on the peptide is converted to aspartic acid, but otherwise the protein remains intact. This deglycosylation leads only to the detection of N-linked glycosylation. The molecular weight of α-glucuronidase was approx. 107,000 before deglycosylation and approx. 95,000 after N-deglycobsylation. After deglycosylation several minor bands (lanes 2, 3 and 4) were observed which could indicate that there are more than one glycosylation site in the enzyme. Accordingly, the extra bands could be the result of an incomplete deglycosylation of such sites. No attempts were made to detect a possible O-linked glycosylation.

Considering the significant glycosylation it was attempted to apply lectin affinity chromatography during the purification, but the concanavalin column tested did not result in purification.

2.4. Isoelectric Point

The isoelectric point for α-glucuronidase was determined by isoelectric focusing (see FIG. 6) to be just below pH 5.2 (positioned just below the β-lactoglobulin A standard, pI 5.2). This is in good agreement with the value of pH 5.3 which was determined by chromatofocusing for the two intracellular α-glucuronidases from *A. niger* by Uchida et al. (1992).

2.5. Temperature Stability

At pH 5 the purified α-glucuronidase was 100% stable at 10° C., for 20 hours, at 45° C. the recovery was 88%, at 50° C. it was 70%, at 55° C. the recovery was 52% and after the 20 hours at 60° C. 10% of the α-glucuronidase activity remained.

During the work with the enzyme we never observed any loss during freezing. At room temperature there was basically also no loss (compare however with the results for pH stability).

2.6. pH Optimum

The pH optimum of the purified α-glucuronidase was between 4.5 to 6 (in 0.1 M Na—Ac buffers), with the highest activity at pH 5 (see FIG. 7). It was found that the activity in the assay was very dependent on the buffer used. It is known that citrate and phosphate (above 25 mM) inhibit colour development in the Milner and Avigad assay (Khandke et al., 1989). Shao et al. (1995) determined the molar extinction coefficients of glucuronic acid in a number of buffers and found that several other buffers also affect the colour development. The pH optimum was therefore determined in Na—Ac buffer, even though this buffer does not buffer optimally in the tested pH range.

2.7. Hydrolysis Products

The purified α-glucuronidase was capable of releasing small amounts of glucuronic acid or methylglucuronic acid from birch wood xylan and wheat bran. However, the enzyme showed a much higher specific activity towards oligomers than towards high molecular weight substrate.

To get a more detailed picture of the hydrolysis, the soluble fractions obtained after 3 hours of hydrolysis of birch wood xylan with α-glucuronidase alone and in all possible combinations with (i) a pure xylanase 1, (ii) a xylanase complex (#1303) and (iii) β-xylosidase, respectively were analyzed for low molecular weight carbohydrates by Dionex HPAEC (see FIGS. 8a–k). In Table 1.2 the quantitative values of xylose, xylobiose and xylotriose as determined by the Dionex HPLC analysis is shown together with the amounts of (methyl)glucuronic acid determined by the calorimetric method (the calorimetric assay is more sensitive than the HPLC method).

Figure 8A:
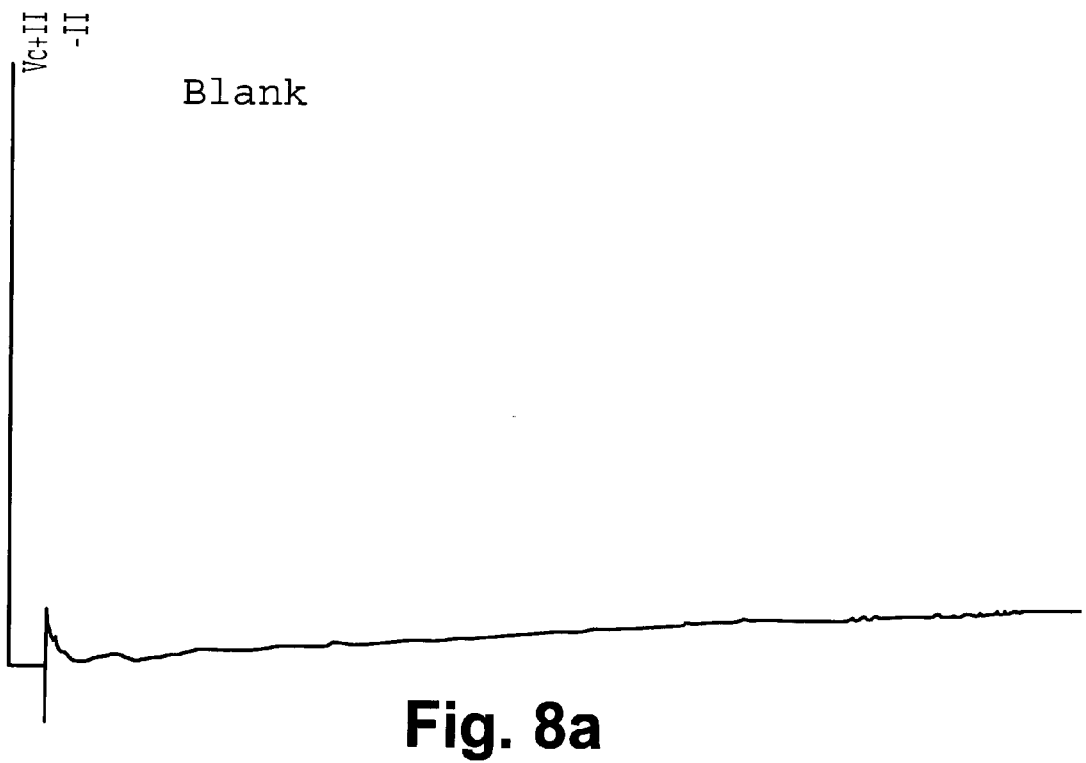
Figure 8B:
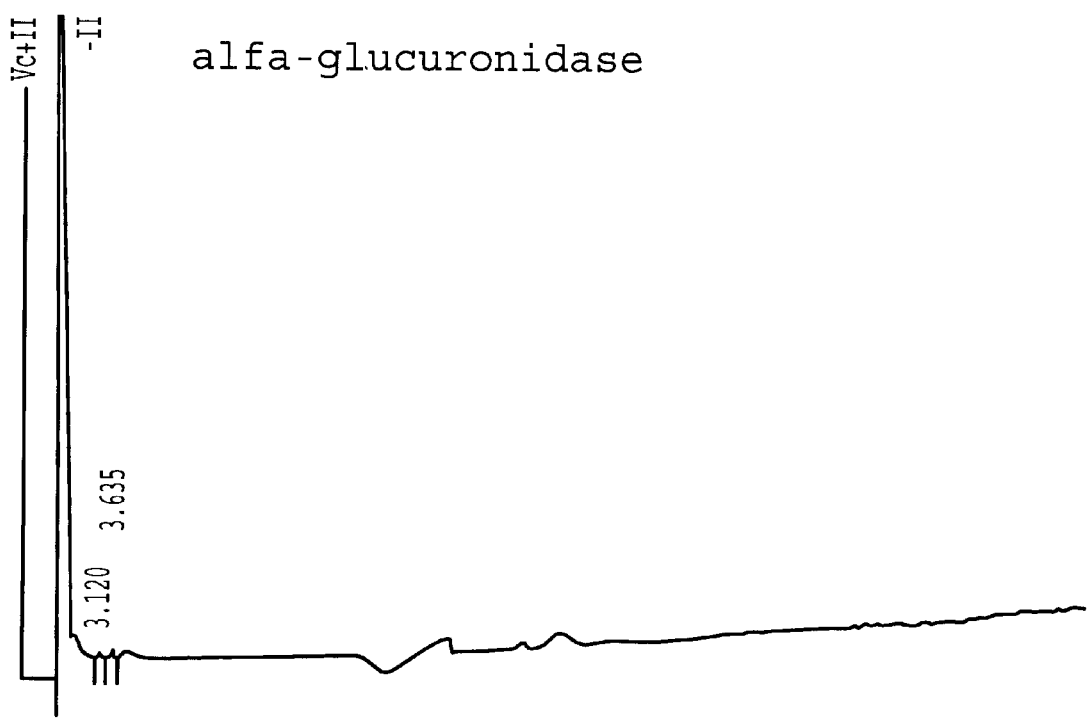
Figure 8C:
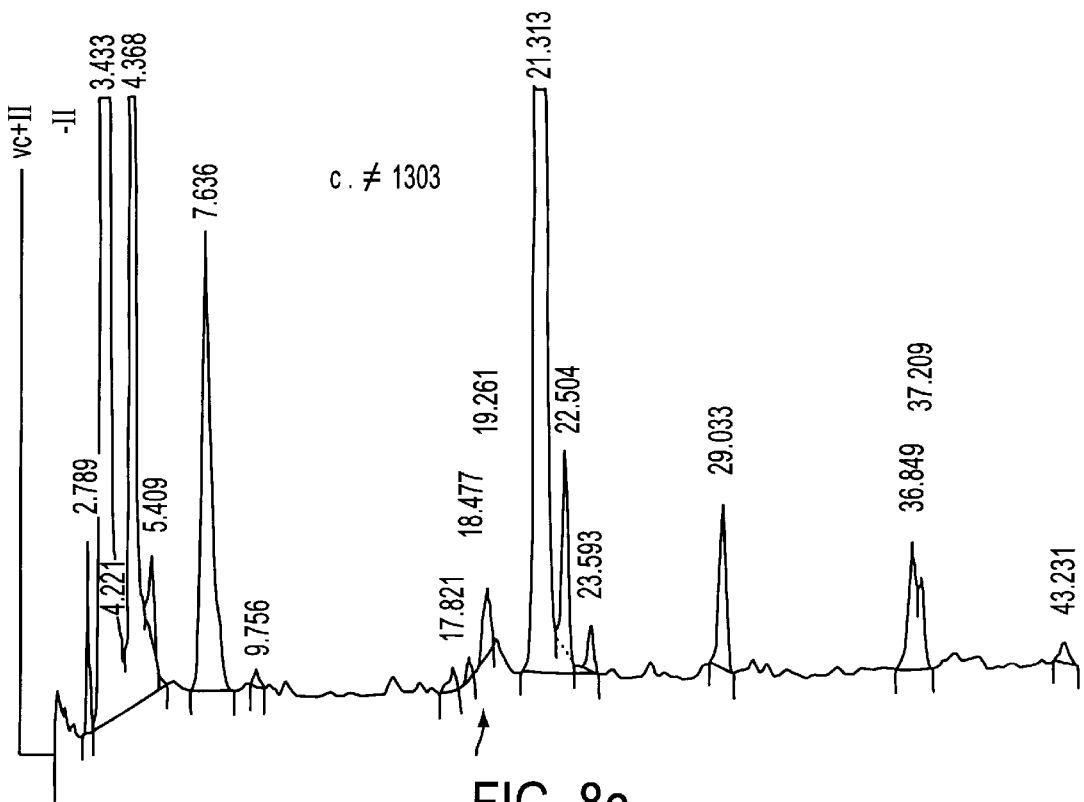
Figure 8D:
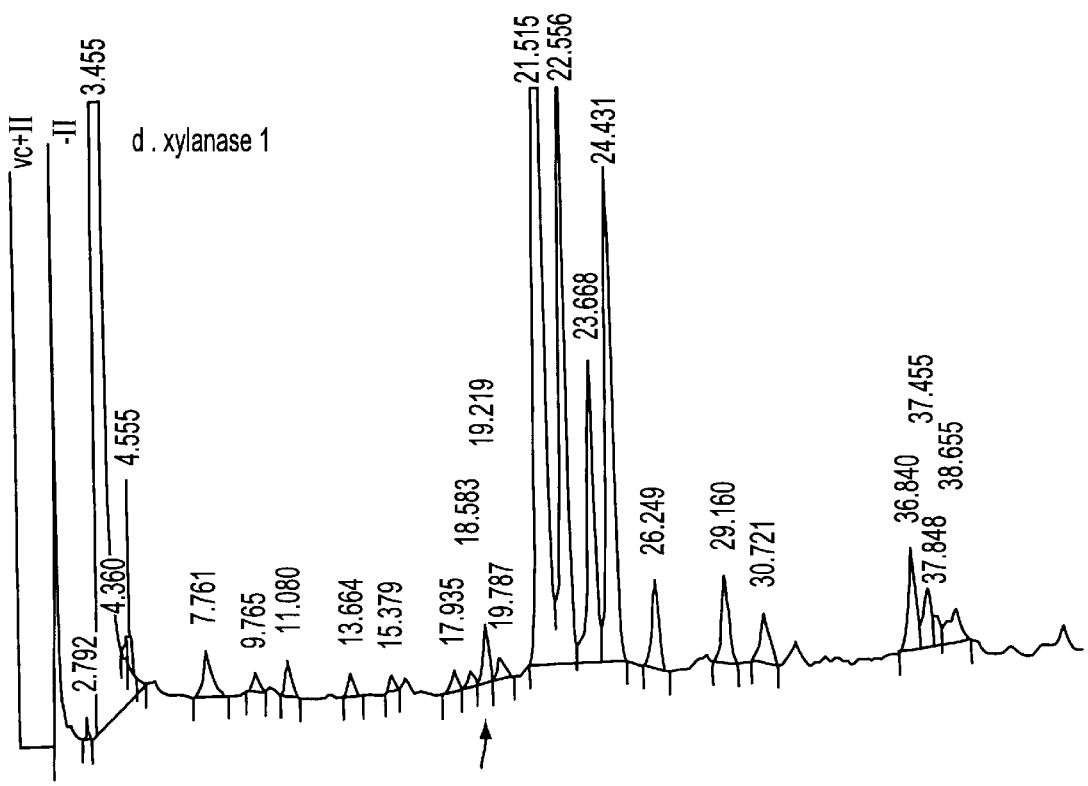
Figure 8E:
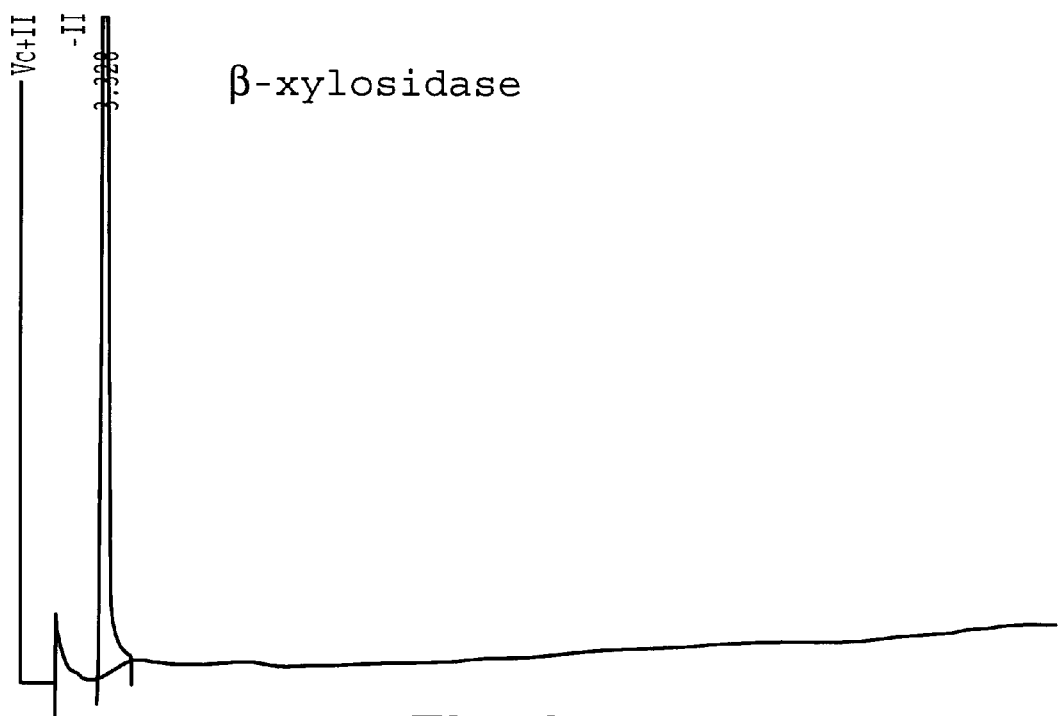
Figure 8F:
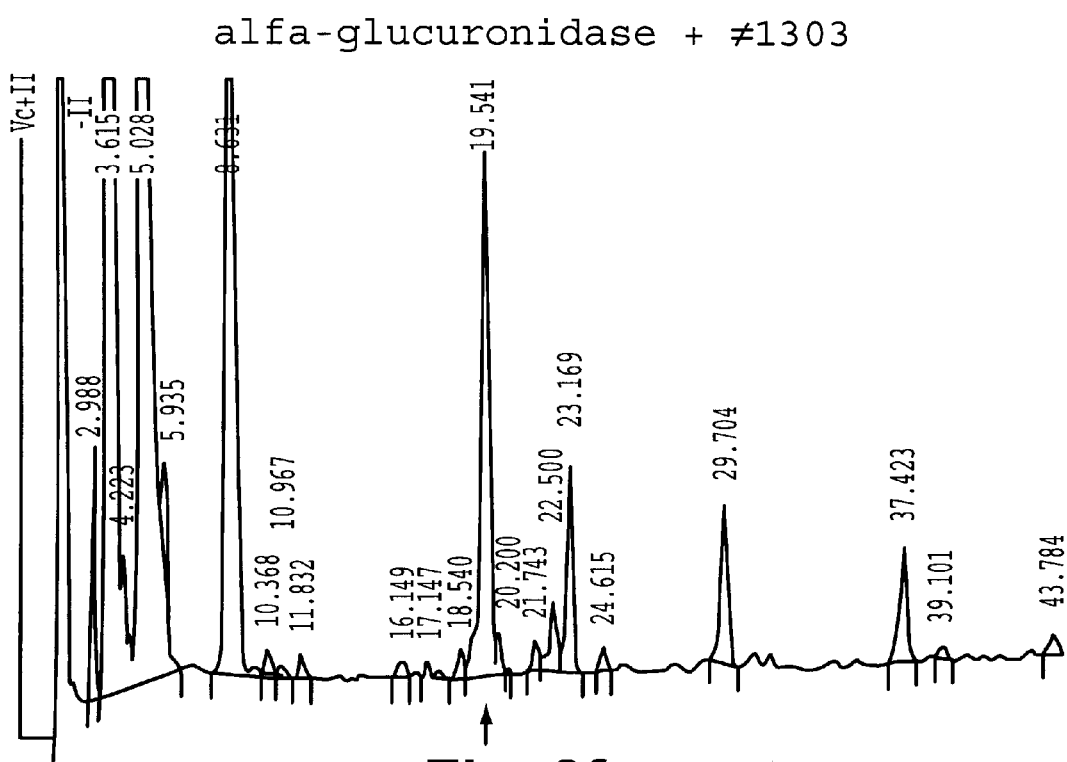
Figure 8G:
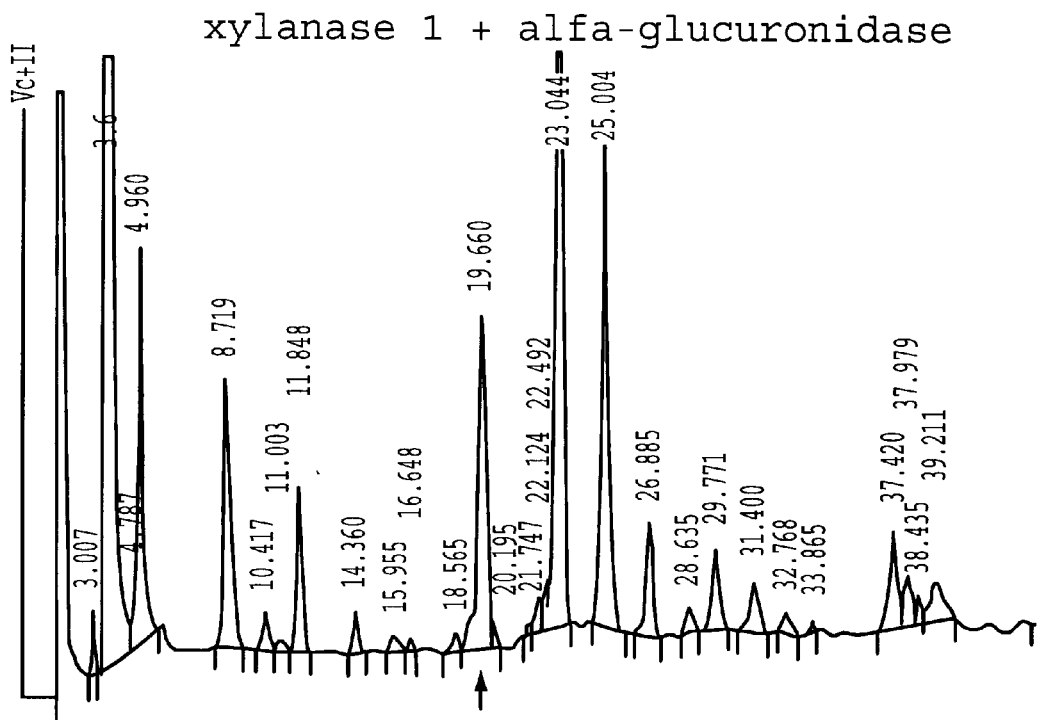
Figure 8H:
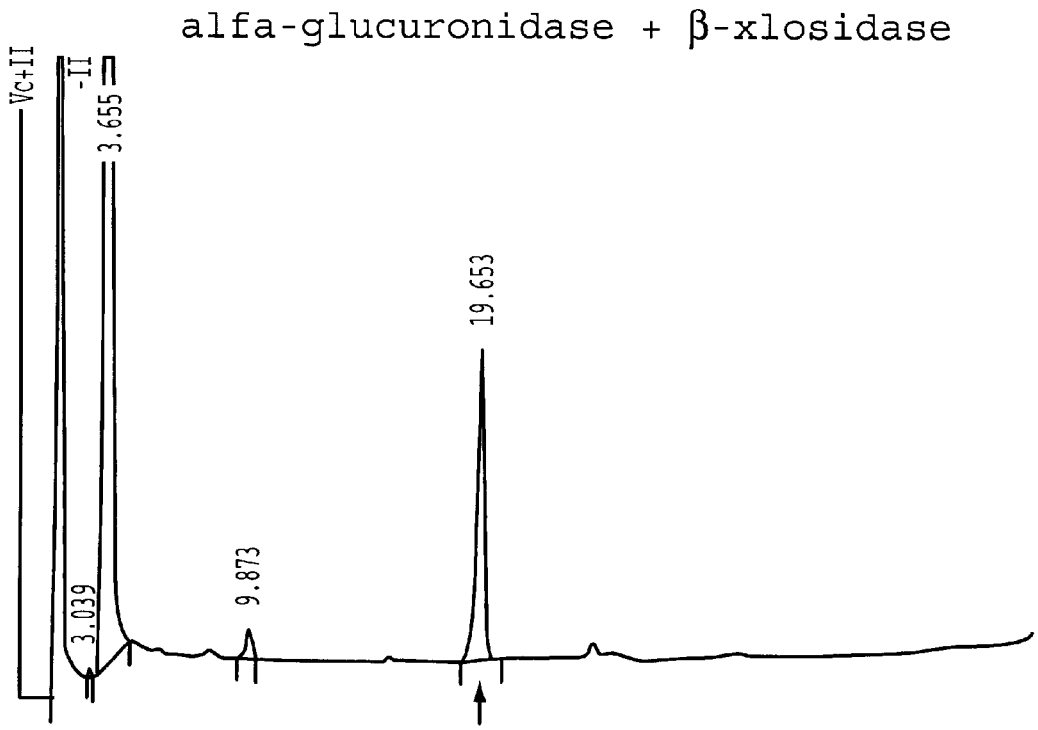
Figure 8I:
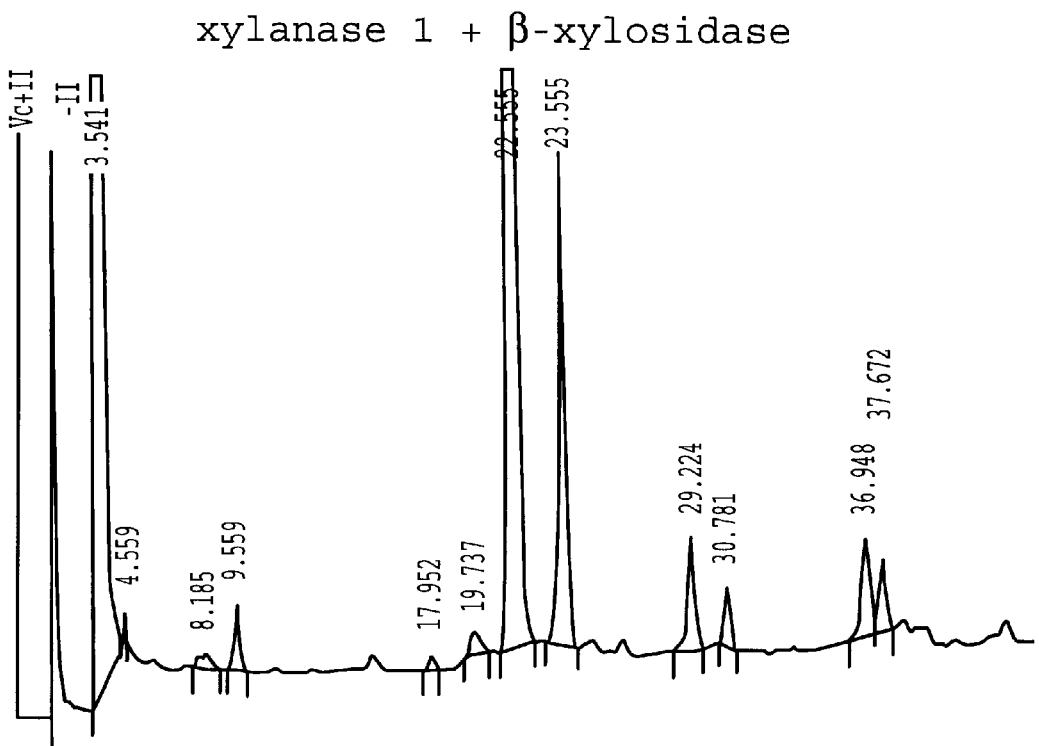
Figure 8J:
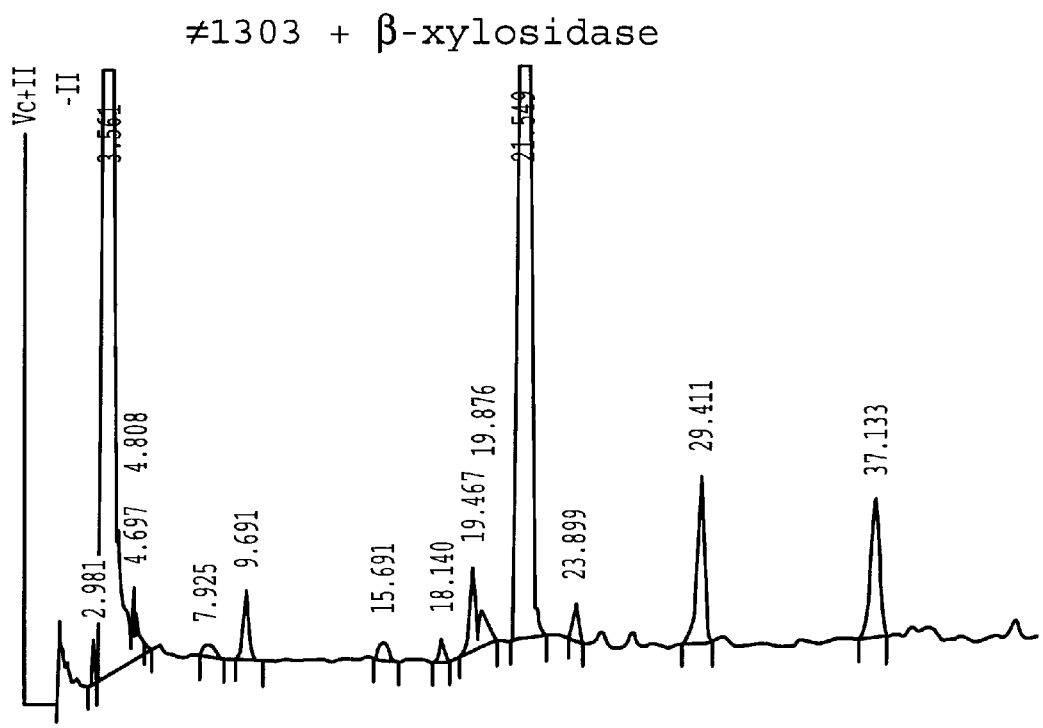
Figure 8K:
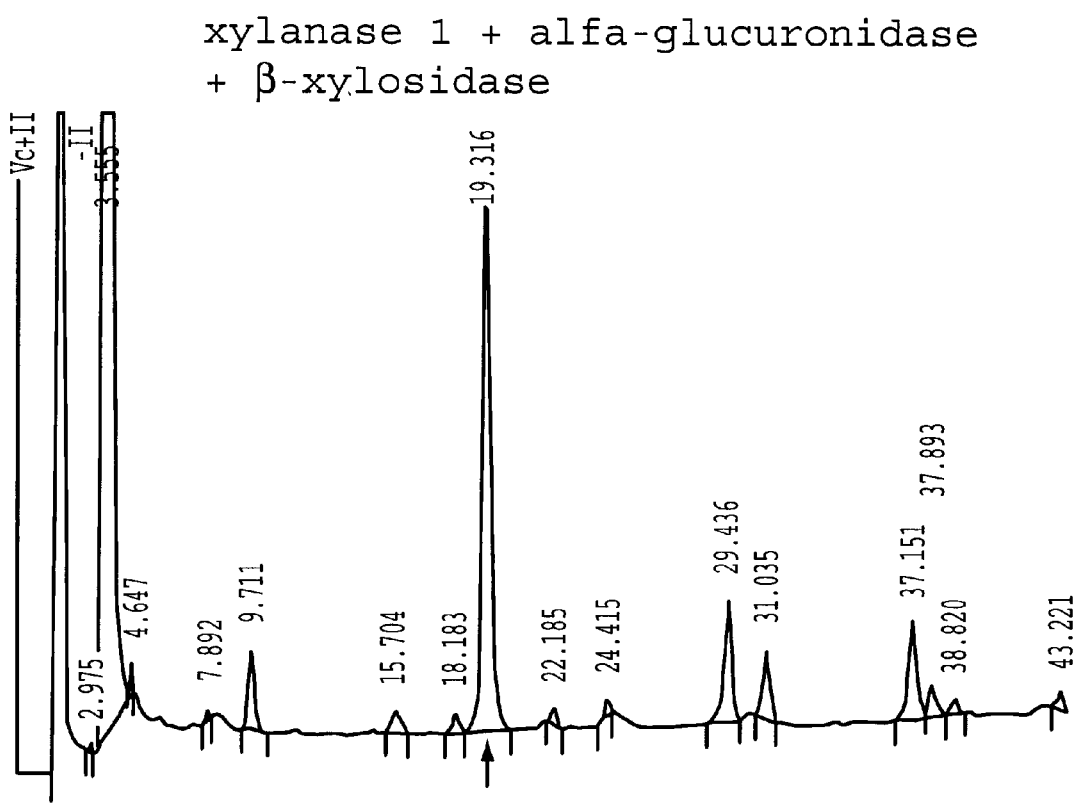
Figure 9:
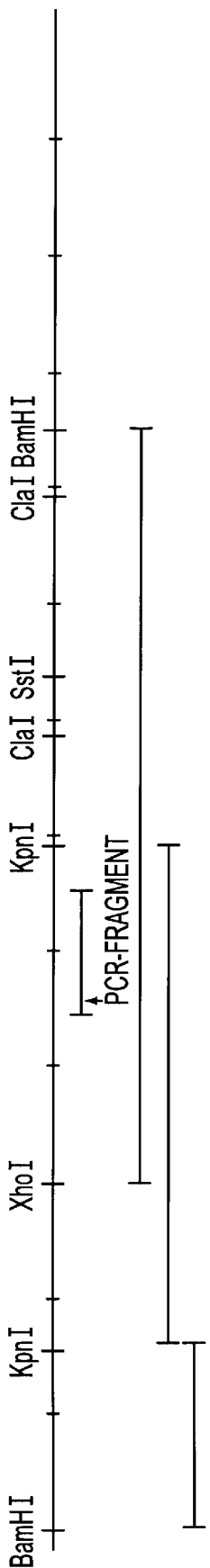

From FIG. 8c it appears how the xylanase complex (which has a very low α-glucuronidase activity) breaks down the birch wood xylan to xylose, xylobiose, xylotriose and a small amount of xylotetraose. Furthermore, there is an accumulation of glucuronylated xylooligomers (retention times from 21 to 25 min) and the small amount of methylglucuronic acid liberated elutes at 19.261 min. From this result it is confirmed that even a complex mixture of xylanases can not completely break down glucuronoxylan to monomeric sugars.

A purified xylanase 1 (see FIG. 8d) can, as it could be expected, hydrolyse less of the substrate than the xylanase complex. From FIGS. 8f and 8g the synergistic effect of xylanases and α-glucuronidase is apparent, since the amount of methylglucuronic acid (retention time 19.541 and 19.660, respectively) is very large as compared to the values in FIG. 8b. There was also an enhancing effect of α-glucuronidase on xylanase activity (compare FIGS. 8c and 8d and FIGS. 8f and 8g). The glucuronoxylooligomers are now hydrolysed to xylooligomers, a quantification of this is given in the below Table 1.2.

TABLE 1.2

Quantification of xylooligomers (µg/µl) and free (methyl)glucuronic acid (arbitrary units) in samples from FIG. 8.

| | methyl glucuronic acid | xylose | xylo biose | xylo triose |
|---|---|---|---|---|
| a. Blank | 299 | 0 | 0 | 0 |
| b. α-glucuronidase | 297 | 0 | 0 | 0 |
| c. #1303 | 609 | 1260 | 440 | 129 |
| d. xylanase 1 | 452 | 1300 | <50 | <50 |
| e. β-xylosidase | 301 | 270 | 0 | 0 |
| f. α-glucuronidase + #1303 | 1811 | 1210 | 680 | 210 |
| g. α-glucuronidase + xylanase 1 | 983 | 1360 | 60 | 70 |
| h. α-glucuronidase + β-xylosidase | 893 | 1060 | <50 | <50 |
| i. xylanase 1 + β-xylo-sidase | 511 | 1320 | <50 | <50 |
| j. #1303 + β-xylosidase | 697 | 1410 | <50 | <50 |
| k. α-glucuronidase + xylanase 1 + β-xylosidase | 1902 | 1500 | <50 | <50 |

Adding α-glucuronidase to a xylanase complex (#1303) gave rise to a slightly increased xylanase activity, see Table 1.3 below.

TABLE 1.3

Xylanase activity as a function of α-glucuronidase addition.

| | Xylanase activity (OD$_{600}$) |
|---|---|
| Blank | 0.114 |
| 0.16 units α-glucuronidase | 0.122 |
| 8 GPU xylanase (#1303) | 0.380 |
| 8 GPU xylanase (#1303) + 0.16 units α-glucuronidase | 0.411 |
| 16 GPU xylanase (#1303) | 0.871 |
| 16 GPU xylanase (#1303) + 0.16 units α-glucuronidase | 0.942 |

The effect of xylanases on the release of glucuronic acid by the α-glucuronridase can be attributed to the preference of α-glucuronidase for the shorter fragments generated by the xylanase, whereas the action of α-glucuronidase in releasing glucuronic acid from the xylan backbone could facilitate the accessibility of the main chain to the xylanase, thereby extending the xylan hydrolysis. There is therefore a reciprocal co-operation or synergy between xylanases and α-glucuronidase.

2.8. Kinetics

Aldotriuronic acid/aldobiuronic acid (approximately 80:20) was used as a substrate for enzyme assay in which glucuronic acid liberated from the substrate was measured. From these results the $K_m$ was calculated using the EZ-FIT curve-fitting microcomputer program (Perrella, 1988). The enzyme showed normal Michaelis-Menten kinetics with respect to aldotriuronic acid. $K_m$ was determined to be 0.14 mg/ml±0.03 mg/ml.

2.9. Amino Acid Sequences

The N-terminal sequence was obtained both by direct N-terminal sequencing and by sequence analysis of individual peptides resulting from digestion of α-glucuronidase. The response factors were very good for the sequence analysis of the peptides. There was a small discrepancy between the N-terminal and peptide 1 but peptide 1 is assumed to be the more correct sequence, since a rather low amount of enzyme for the N-terminal sequencing was available.

N-terminal:
EDGYDGWLRYAPVHRDLH (SEQ ID NO:1)
Peptide 1:
XDGYDGWLRYAPVSCDLHCRQALPSHIVLLXSTK (SEQ ID NO: 9)
Residue No 1 is either C or E, most likely E
Peptide 2:
AGFQSILSTXLTSHPFQ(C/E)DSSASILVATLD(E)YRQK (SEQ ID NO: 10)
The two residues in parsentheses were uncertain.
Peptide 3:
II/KGEADGVEPAPVDYVV(LLPKGK) (SEQ ID NO:11)
The last six residues (LLPKGK) are possible but uncertain whereas the remaining residues are very certain (very high response factors). Residues 6 and 18 are potential glycosylation sites.
Peptide 4:
APSGVYDIGVNYYDLYGGQSK (SEQ ID NO:5)
Peptide 5:
YGPIDFQVREPTSPLFANLYQT-NTAIELEVSQEYLGQQCH (SEQ ID NO: 6)
Peptide 6:
WTLSVGDK (SEQ ID NO: 7)
Peptide 7:
TVLDFDLRVDHKPSMVRDIISGQR-FXRTLGGWAAVVNVGTXR (SEQ ID NO: 8)

2.10. Conclusions

An extracellular α-glucuronidase has for the first time been purified from an *Aspergillus niger*-derived crude enzyme source. The present extracellular α-glucuronidase from *A. niger* appears to be very different from the two intracellular *A. niger* α-glucuronidases previously isolated and characterized by Uchida et al. (1992).

To our knowledge this is the first report of amino acid sequence data for an α-glucuronidase.

EXAMPLE 2

The in vitro Activity of Native α-glucuronidase Using Wheat as the Substrate Under Conditions Simulating those of the Digestive Tract of Poultry The purpose of this experiment was to study the effect of purified, native α-glucuronidase as a viscosity reducing agent in chicken feed and the effect on residual dry matter of feed.

2.1 Test Enzyme

An enzyme preparation prepared as described in Example 1 and having an enzymatic activity of 1.95 α-glucuronidase units per ml was used.

2.2. Reagents 1.1. 0.015 M HCl
1.2. 0.50 M HCl
1.3. 0.2 M phosphate buffer, pH 7.00 (10.8 g $NaH_2PO_4.1 H_2O$+21.7 g $Na_2HPO_4.2 H_2O$ /1000 ml)
1.4 Pepsin, Merck 1.07190, 2.5 g/50 ml phosphate buffer
1.5. Pancreatin, Sigma P-7545 2.5 g/50 ml phosphate buffer 2.3. Substrate 10.0 g of ground wheat 2.4. Experimental Protocol All reaction steps were carried out at about 40° C. in 50 ml blue cap bottles under stirring.

The substrate wheat was weighed into a 50 ml blue, cap bottle and 1.0 ml enzyme preparation+2 ml distilled water and 15.5 ml 0.015 M HCl was added to provide a homogeneous suspension of the wheat. The mixture was kept 1 hour at 40° C. on a Vario-mag™ Telemodul 40S at the positions: NORMAL/STIR/500 RPM.

Subsequently, 4 ml 0.5 M HCl and 5 ml pepsin solution was added and the mixture was kept for 1.5 h following which 6.0 ml 0.2 M phosphate buffer, 5 ml pancreatin solution and 100 μl of a 5% solution of chloramphenicol in EtOH was added and the mixture allowed to stand for an additional 3 h.

In the next step, the reaction mixture was centrifuged at 2500 rpm for 10 min. The supernatant was decanted and 10 ml collected and heated in a boiling water-bath for 5 min. Six ml was filtered using a 0.45 μm filter and the viscosity of the filtrate was measured at 50° C. using an Ostwald viscosimeter No. 25 and 5 ml of sample.

The pellet was suspended in 25 ml phosphate buffer and 5 ml pancreatin solution was added with 100 μl 5% chloramphenicol solution. The mixture was allowed to stand under stirring for 18 hours at 40° C. followed by centrifugation at 2500 rpm for 10 min. The supernatant was discarded and the pellet resuspended in 40 ml distilled water and left to stand under stirring for 5 min. Centrifugation at 2500 rpm for 10 min after which the supernatant was discarded, and this step was repeated. The final pellet was frozen in liquid nitrogen and freeze-dried for 24 h before weighing and used for determination of residual dry matter.

In a control experiment 3 ml distilled water was used in place of the enzyme preparation+distilled water.

2.5 Results and Conclusions

With respect to viscosity reduction, the results were 0.74 mini for distilled water 2.24 min for the control sample without enzyme addition and 2.10 min for the test sample. It could thus be concluded that the addition of α-glucuronidase to a wheat substrate only had a very low viscosity reducing effect.

The results of the determinations of residual dry matter showed a weight of the pellet resulting from the control experiment of 2.7328 g and for the test sample, the corresponding weight was 2.4312 g, i.e. a reduction in residual dry matter of about 11% which is an indication that the α-glucuronidase preparation enhances the digestibility of cereal feedstuffs.

The above experiment was repeated using corn cob meal in place of grounded wheat. The results were essentially the same as with wheat as substrate.

EXAMPLE 3
Use of Purified Native α-glucuronidase to Release Metal Ions from the Dietary Fiber Fraction of Food and Feed α-Glucuronidase side groups present in the hemicellulose of the dietary fiber fraction in both feed and food represent a negative charge. The counter ion at the intestinal pH must be a positively charged cation and it has been disclosed that dietary fibers may affect the mineral bioavailability (Idouraine et al. 1995).

In this experiment it was demonstrated that there is an increased release of $Ca^{2+}$ and $Mg^{2+}$ in a dialysable (and assumingly bioavailable) form from chicken feed when this is treated with the purified α-glucuronidase according to the invention.

The enzyme preparation used was prepared as described in Example 1 (containing 1.6 α-glucuronidase units/ml) and desalted in 20 mM, Na—Ac, pH 5.0. A suspension of 1.0 g of a chicken feed composition suspended in 4.15 ml 20 mM Na—Ac, pH 5.0 and 0.85 ml of the α-glucuronidase preparation was added to a pre-wetted Servapore™ #44145 dialysis tube (diameter 16 mm, length 150 mm) and placed in a acid washed cleaned beaker containing 200 ml deionized water. As a control, a feed suspension in 5 ml of thee buffer was used. The dialysis was carried out for 26 hours and the content of metal ions in the dialysate determined by flame ionization spectrometry.

The results are summarized in Table 3.1

TABLE 3.1

The effect of α-glucuronidase on release of divalent cations (ppm) from chicken feed.

|  | $Ca^{2+}$ | $Mg^{2+}$ |
| --- | --- | --- |
| Control | 10 | 2.4 |
| α-Glucuronidase | 23 | 3.9 |

EXAMPLE 4
Construction of a Genomic Library of *Aspergillus tubigensis* Strain NW756

The *Aspergillus tubigensis* NW756 genomic library as described by Bussink et al. (1991) was constructed by ligating partially Sau3A1-digested genomic DNA fragments into the phage lambda replacement vector EMBL3 cut with BamHI.

EXAMPLE 5
Screening of the *Aspergillus tubigensis* Genomic Library for the α-alucuronidase Gene (aguA) and Isolation of the Gene 5.1. Isolating an aguA Fragment Using PCR with Synthetic Oligonucleotide Mixtures Details of molecular cloning techniques are described by Sambrook et al. in Molecular Cloning: A Laboratory Manual, 2nd edition (1989; Cold Spring Harbor Laboratory Press).

The amino acid sequences derived in Example 1 were used to synthesize degenerate oligonucleotide mixtures. The oligonucleotides were synthesized using an Applied Biosystems 392 DNA/RNA Synthesizer in accordance with the recommendations of the manufacturer.

PCR reactions were performed using an equal amount of two oligonucleotide mixtures, Taq-polymerase (BRL) and 20 ng of chromosomal DNA of *Aspergillus tubigensis* NW756. The denaturing temperature was 95° C. for one minute, the annealing temperature was 55° C. for one minute and the extension temperature was 72° C. for one minute. 30 cycles were applied.

The reaction mixture was subjected to agarose gel electrophoresis. The reaction using a downstream oligonucleotide based on peptide 5 (agu-5) and an upstream oligonucleotide based on peptide 4 (agu-9) resulted in a 1.1 kb fragment. This fragment was isolated from gel using the GeneClean method (Bio101 Inc., USA). The used oligonucleotides had the following sequences:

agu-5' (downstream oligonucleotide mixture based on peptide 5)

```
5'-ggaccaatagacttccaagt-3' (SEQ ID NO:12)
    c  c  c  t  t  g
    g  g  t
    t  t
``` agu-9 (upstream oligonucleotide mixture based on peptide 4)

```
5'-aaatcataataattaacacc-3' (SEQ ID NO:16)
   gg g  g  g  c  c
         g  g
         t  t
```

5.2. Cloning and Sequencing of the 1.1 kb aguA Fragment

The DNA fragment isolated above was cloned in the pGEM-T Vector system (Promega Biotech Inc.). Sequence analysis of this fragment was performed using a T7-sequencing kit (Pharmacia). This resulted in a single strand sequence in which both of the oligonucleotide sequences could be detected.

The complete nucleic acid sequence of this fragment was transformed into a putative amino acid sequence. Peptide 4 and 5 on which the oligonucleotides were designed could be identified and a third amino acid sequence (peptide 7, Example 1) showed complete identity to a internal region of the sequence.

5.3. Screening of the *Aspergillus tubigensis* Genomic Library for the aguA Gene For the screening of the *A. tubigensis* genomic library, $2.4 \times 10^3$ pfu per plate were plated on five plates of 15 cm diameter using *E. coli* LE 392 as plating bacterium. LM (10 g/l tryptone, 5 g/l yeast extract, 10 mM NaCl, 10 mM $MgCl_2$) medium plus 1.5% agar or 0.6% agarose were used for the bottom and top layer, respectively.

After overnight incubation of the plates at 37° C., duplicate filters (Hybond-N, Amersham) were prepared from each plate. The DNA was cross-linked to the filters by UV-treatment for 2 minutes. The filters were then pre-hybridized for three hours and screened with the 1142 bp aguA fragment using hybridization and washing conditions similar for those used for Southern blot hybridizations (hybridization temperature was 65° C., washing conditions were 2×20 minutes in 2×SSC, 0.5% SDS followed by 2×20 minutes in 0.2×SSC, 0.5% SDS).

Six positive phages were isolated from the plate using a Pasteur pipette and the phages were eluted from the agar plug in 500 ml SM buffer, containing 10 μl chloroform. The phages obtained were purified using the procedure described above with duplicate filters from plates each containing 50–100 plaques of the phages isolated.

After purification, the phages were propagated by plating out until confluent plates were obtained. The phages were eluted by adding 3 ml SM buffer and intermittent shaking for two hours. The buffer containing the phages was transferred to Eppendorf tubes and centrifuged for 5 minutes at maximum speed in an Eppendorf centrifuge to remove bacteria. The supernatant was transferred to a new Eppendorf tube, 20 µl chloroform was added and the number of pfu was determined. These phage stocks contained approximately $5 \times 10^{10}$ pfu/ml.

5.4. Restriction Analysis of aguA-containing Phages

From each of the isolated phages, DNA was isolated according to Sambrook et al., supra. The isolated DNA was analyzed by Southern analysis using the following restriction enzymes: BamHI; BglII; ClaI; ECORI; ECORV; PstI; SmaI and XhoI in single and double digestions. The DNA was digested for four hours at 37° C. After digestion the fragments were separated by agarose gel electrophoresis at 50 V for 6 hours.

After electrophoresis, the DNA was denatured and transferred to a nitro-cellulose membrane (Hybond-N, Amersham). Prehybridization, hybridization and washing were performed as described above.

In this way preliminary restriction maps were constructed (see FIG. 9) and fragments hybridizing to the 1142 bp aguA fragment were selected for cloning.

EXAMPLE 6
Subcloning of the augA Gene

DNA fragments from the isolated phages described above were selected for subcloning of the aguA gene. 20 µg of phage DNA was digested for four hours with 50 units of the selected restriction enzymes at 37° C. The fragments were separated by agarose gel electrophoresis and isolated by the GeneClean method (Bio101 Inc.).

The fragments were ligated in the vector pbluescript SK+ cut with the corresponding enzyme. Ligations were performed overnight at 16° C. with T4 DNA-ligase (BRL). The ligation mixtures were transferred to E. coli DH5α and grown overnight on LB (10 g/l NaCl, 10 g/l Tryptone, 5 g/l yeast extract, 1.5% agar) plates containing 50 µg/ml ampicillin, 0.1% X-gal and 5 mM IPTG.

Per ligation, 5 white transformants were selected and grown overnight in 5 ml LB (10 g/l NaCl, 10 g/l Tryptone, 5 g/l Yeast Extract) medium at 37° C.

Plasmid DNA was isolated from the cultures by the alkaline lysis method (Sambrook et al., supra).

A culture of phage lambda containing aguA was deposited on May 3, 1996 with the National Collections of Industrial and Marine Bacteria Ltd. (NCIMB), 23 St. Machar Drive, Aberdeen AB2 1RY, Scotland under the Accession No. NCIMB 40801.

EXAMPLE 7
Sequencing of the aguA Gene

The sequence of the A. tubigensis aguA gene was determined by sequencing the subcloned fragments. Sequencing was performed using the Thermo Sequenase fluorescent labelled primer cycle sequencing kit (Amersham LIFE SCIENCE) and the ALF express (Pharmacia Biotech).

The sequences obtained were analyzed with the PC Gene software (IntelliGenetics) resulting in a structural gene of 2579 bp (see FIG. 10).

EXAMPLE 8
Transformation of Agpercillus tubigensis with the aguA Gene

A. tubigensis can be transformed with the α-glucuronidase gene using the transformation procedure of de Graaff et al. (1992). Alternatively, the transformation of A. tubigensis can be based on the teachings of Buxton et al. 1985 (Transformation of Aspergillus niger using the argB gene of Aspergillus nidulans. Gene 37:207–214), Daboussi et al. 1989 (Transformation of seven species of filamentous fungi using the nitrate reductase gene of Aspergillus nidulans.; Curr. Genet. 15:453–456), Punt et al. 1992 (Transformation of filamentous fungi based on hygromycin B and Phleomycin resistance markers. Meth. Enzymol. 216:447–457).

Protoplasts were prepared from mycelium by growing Aspergillus tubigensis NW756 on minimal medium supplemented with 50 mM glucose, 0.5% yeast extract, 0.2 % casamino acids and 10 mM uridine for 20 hours at 30° C. The minimal medium had the following composition (per 1000 ml): 6.0 g NaNO$_3$, 1.5 g KH$_2$PO$_4$, 0.5 g MgSO$_4$.7H$_2$O, 0.5 g KCl, 1 ml Visniac solution (Visniac, W., Santer, M. 1957 Bact. Rev. 21:195), pH 6.0. The preparation of protoplasts of A. tubigensis NW756 and the transformation procedure was performed as described by Harmsen, J. A. M., Kusters-van Someren, M. A., Visser, J. (1990).

EXAMPLE 9
Screening of Other Aspercillus Species for the Presence of the aguA Gene Chromosomal DNA was isolated from A. niger N400 (CBS 120.49), A. nidulans WG096, A. tubigensis NW756, A. niger var. awamori 407.9 (CBS 115.52), A. aculeatus 489.16 (CBS 610.78),A. japonicus (CBS 114.51);,A. oryzae 422.5 (ATCC 203.86), A. sojae 363.9 (ATCC 202.35), A. carbonarius 277.11 (CBS 420.64) and A. niger 3M43 (Grindsted Products A/S collection).

3 µg of DNA was digested with HindIII, separated on agarose gel electrophoresis and transferred to a nitrocellulose membrane. Southern hybridization was performed on the filter with the 1142 bp aguA-fragment at 56° C. The filter was washed 3×20 minutes with 4×SSC, 0.5% SDS.

All species tested showed hybridizing bands with the 1142 bp aguA fragment, indicating the presence of similar genes in all these fungal species.

EXAMPLE 10
Production of Antibodies Against α-glucuronidase

200 µg of α-glucuronidase was dialysed against 1 mM phosphate buffer, pH 7.0 and freeze-dried. The protein was resuspended in 400 µl sterile PBS: (0.136 M NaCl, 2.7 mM KCl, 8 mM Na$_2$HPO$_4$, 1.75 mM KH$_2$PO$_4$, pH 7.4). To 100 µl of this protein mixture, 100 µl Freunds' complete adjuvant was added and vortexed for 30 minutes to obtain a stable emulsion. This mixture was injected into a mouse subcutaneously. In week 4 a booster was given by injecting 50 µl of the protein mixture, 50 µl PBS and 100 µl of Freunds' incomplete adjuvant. The mouse was bled in week 5 and the serum was tested. In week 9 a second booster was given followed by a bleeding in week 10.

This procedure of boosters with an interval of 4 weeks followed by a bleeding may be repeated several times.

The collected blood was stored at 4° C. for 16 hours. After centrifugation the serum was collected.

EXAMPLE 11
Construction of an α-glucuronidase (AGUA) Overproducing Strain

A construct, pIM3212 was made which contained the structural aguA gene isolated from Aspergillus tubigensis, 2.7 kb of the 5'-flanking region and 2 kb of the 3'-flanking region. The construct was made in a two step procedure where a 6.5 kb XhoI/BamHI fragment was cloned into pBluescript SK+ resulting in plasmid pIM3210. This plasmid was cut with KpnI (removing 2.5 kb of the insert) and a 4 kb KpnI fragment was ligated into the construct resulting in the plasmid pIM3212 (see FIG. 12).

The *Aspergillus niger* strain NW241 which is a pyrA negative mutant of strain 3M43 (Grindsted Products A/S Collection) was transformed with plasmid pIM3212. The transformant with the highest level of AGUA when grown on birchwood xylan, transformant NW241::pIM3212.8 was selected for further experiments. Southern analysis of chromosomal DNA of this transformant revealed the presence of about 20 copies of the aguA gene.

A sample of the above, pIM3212.8 has been submitted for depositing under the Budapest Treaty with the National Collections of Industrial and Marine Bacteria Ltd. (NCIMB), 23 St. Machar Drive, Aberdeen AB2 1RY, Scotland.

EXAMPLE 12

The aguA Gene is Regulated by the Xylanolytic Regulator Gene xlnR

A xlnR negative *Aspergillus niger* mutant strain (WO 97/00692) was used to study the effect of this regulator on the expression of the agua gene. This strain and an *Aspergillus niger* wild-type strain were grown overnight on minimal medium supplemented with 1 wt % of fructose. The mycelium was transferred to minimal medium containing 1 wt % birchwood xylan and incubated for another 5.5 hours. The mycelium was harvested, RNA was isolated and a Northern analysis was performed.

In the wild-type strain the transfer to the xylan-containing medium resulted in the expression of the aquA gene whereas in the mutant strain no expression could be detected, indicating a strong influence of xlnR on the induction of aguA.

Step 2. The resulting enzyme solution was subjected to hydrophobic interaction chromatography using a 20 ml Source HIC, phenyl column, 1.6 cm×10 cm (Pharmacia) equilibrated in phenyl sepharose buffer (20 mM Na-acetate, 1.5 M $(NH_4)_2SO_4$, pH 5.0). The column was washed with phenyl sepharose buffer. α-glucuronidase was eluted using a 300 ml gradient from 1.5 to 0 M of $(NH_4)_2SO_4$ in 20 ml Na-acetate, pH 5.0 at a flow rate of 5 ml/min. Fractions 22 and 23 each of 7.5 ml containing the α-glucuronidase activity were pooled.

Step 3. The pooled fractions were desalted in PD 10 columns equilibrated in a buffer A containing 20 mM triethanolamine, pH 7.3 and 1 mM $CaCl_2$, and loaded onto 1 ml Source Q10 (HR5/5) (Pharmacia) equilibrated in buffer A. After washing with 10 ml of buffer A α-glucuronidase was eluted with a linear salt gradient from 0 to 0.5 M NaCl in buffer A at a flow rate of 1.5 ml/min, and fractions of 1.5 ml were collected. Fractions 4–6 containing the α-glucuronidase activity were pooled to a total volume of 4.5 ml.

Step 4. The pooled fractions 4–6 were loaded onto a 2 ml Poros Q10 (HR10/5) column (PerSeptive Biosystems) equilibrated in the above buffer A. Elution was carried out with a linear salt gradient of 0–0.5 M NaCl in buffer A. Fractions of 1 ml were collected and screened for α-glucuronidase activity. The purification steps and the results are summarized in Table 13.1.

TABLE 13.1

Purification of recombinant α-glucuronidase

| Step | Volume (ml) | Protein (mg/ml) | Total protein (mg) | U/ml (µmol/-min/ml) | Total activity units | Specific activity (µmol/mg/-min) | Purification fold | Recovery % |
|---|---|---|---|---|---|---|---|---|
| Crude extract | 20 | 0.097 | 1.95 | 1.1 | 22 | 11.3 | 1 | 100 |
| Desalting | 27 | 0.067 | 1.81 | 0.76 | 20.5 | 11.3 | 1 | 93 |
| HIC | 21 | 0.024 | 0.51 | 0.61 | 13 | 2.2 | 2.2 | 59 |
| SourceQ | 4.5 | 0.025 | 0.114 | 0.63 | 2.8 | 25.2 | 2.2 | 13 |
| PorosQ | 5 | 0.0084 | 0.043 | 0.33 | 1.7 | 39.3 | 3.5 | 7.7 |

EXAMPLE 13

Production and Characterization of Recombinant α-glucuronidase 13.1. Production of Recombinant α-glucuronidase Spores of the transformant NW241::pIM3212.8 (Example 11) were collected from PDA-plates after 7 days of incubation at 30° C. The spores (0.5 ml containing $10^6$ spores) were inoculated in 500 ml. shake flasks containing 200 ml of medium containing (w/v): 1.5% $KH_2PO_4$, 0.5% KCl, 1% $MgSO_4$, $7H_2O$, 6% $NaNO_3$ and 1% birchwood xylan. pH was adjusted to 6.0 before autoclaving at 124° C. for 20 min.

Following incubation the flasks were shaken at 200 rpm at 30° C. for 5 days before harvesting over a 0.2 µm filter to remove the mycelium.

13.2. Purification of Recombinant α-glucuronidase

The culture supernatant from NW241::pIM3212.8 cultured as described above was used for the isolation of purified recombinant α-glucuronidase.

Step 1. 20 ml of the supernatant was desalted on PD 10 columns (Pharmacia) equilibrated in 20 mM Na-acetate, pH 5.0 containing 1 mM $CaCl_2$. The resulting volume was 27 ml.

13.3. Molecular Weight of Recombinant α-glucuronidase

Fractions 12–15 resulting from Poros Q10 purification were separated on a Tris-glycine SDS gradient gel (8–16% PAA) using a Novex system. Silver staining revealed one band at an approximate molecular weight of 115 kDa. Deglycosylation using endoglycosidase H (Sigma) as described by the manufacturer of the native enzyme (Example 1) and the recombinant α-glucuronidase gave an approximate molecular weight of 93 kDa for both enzymes, The gel is shown in FIG. 11.

13.4. Matrix-assisted Laser Desorption Ionization (MALDI) Mass Spectrometry of Native and Recombinant Glucuronidase MALDI/TOF mass spectrophotometry was performed using purified native (Example 1) and recombinant α-glucuronidase (this example), respectively mixed with a matrix solution consisting of sinapic acid (3,5-Dimethoxy-4-hydroxy cinnamic acid) in 60% acetonitrile, 0.1% TFA. The mixture was spotted onto a target plate which was air dried and loaded into a Perspective Biosystems Voyager DE mass spectrometer. The molecular mass determined for the desalted recombinant α-glucuronidase was 116 kDa and for the native enzyme 112 kDa. This confirms the above MW approximation obtained by SDS-PAGE.

13.5. Temperature Optimum of the Recombinant α-glucuronidase

The purified recombinant α-glucuronidase activity was measured as described in Example 1 for the native enzyme with incubation for 10 min in 0.05 M Na-acetate buffer, pH 5.0 at 40, 50, 60, 70 and 80° C., respectively. As a reference, the native α-glucuronidase produced and purified under the same conditions as the recombinant enzyme was included. Both recombinant and native α-glucuronidase showed maximum activity at 60° C. At 70° C. the activity was about 80% of the optimum and at 80° C. it was less than 5% of the optimum activity.

13.6. Temperature Stability of Recombinant α-glucuronidase

The experiments were conducted as described in Example 1 for the native α-glucuronidase. Eppendorf tubes with 200 μl of purified recombinant α-glucuronidase preparation were incubated at 45, 50, 55 and 60° C., respectively for 20 hours. As a control a tube was incubated at 10° C. for 20 hours.

The samples were assayed for α-glucuronidase activity as described in Example 1 (Materials and methods). The results are summarized in the below Table 13.2.

TABLE 13.2

Temperature stability of recombinant α-glucuronidase

| Temperature, ° C. | μmol | Residual activity (%) |
|---|---|---|
| 10° C. (control) | 1362 | 100 |
| 45° C. | 1074 | 78 |
| 50° C. | 964 | 71 |
| 55° C. | 701 | 51 |
| 60° C. | 275 | <20* |

*The residual activity determination at 60° C. was influenced by the non-linearity of the standard curve at this OD conducted at 25° C.

13.7. pH Optimum of Recombinant α-glucuronidase

Purified recombinant α-glucuronidase activity was measured as described in Example 1. 100 mM Na-acetate was used in the pH range 3.5 to 6.0. pH values were determined in the assay tubes at room temperature. The pH optimum was between 4.5 and 6.0.

13.8. pH Stability of Recombinant α-glucuronidase

Purified recombinant α-glucuronidase (150 μl) was kept at 35° C. in 500 μl buffer,containing 0.2 M Na-acetate (pH 4.0), 0.2 M bis-Tris (pH 6.0), and 0.2 M Tris (pH 8.0), respectively for 5, 8 and 12 days and the residual activity was measured as described in Example 1. As a reference, native α-glucuronidase produced and purified under the same conditions as the recombinant enzyme was included.

The results confirmed that the native enzyme as well as the recombinant α-glucuronidase are completely stable at pH 6.0 at 12 days of incubation at 35° C. but less stable at pH 8.0.

13.9. Amino Acid Sequencing of Recombinant α-glucuronidase

N-terminal sequencing of the purified, recombinant α-glucuronidase was carried out by direct N-terminal sequencing as described for the native enzyme (Example 1). 30 cycles were conducted using both recombinant and native α-glucuronidase produced and purified under identical conditions. The results are shown below:

N-terminal sequence for the recombinant α-glucuronidase:
EDGYNGWLRYAPVSXDLHXRQALPSHIVLL (SEQ ID NO:20)

N-terminal sequence for the native α-glucuronidase:
EDGYDGWLRYAPVSXDLHXRQALPSHIVLL (SEQ ID NO:21)

The aspartic acid at position 5 of the native protein has been replaced by asparagine in the recombinantly produced protein.

The two X's at the positions 15 and 19 are probably cysteine residues which cannot be detected because they were not derivatized.

13.10. Determination of Specific Activity of Recombinant α-glucuronidase

Specific activity was determined for the purified recombinant and native α-glucuronidase, respectively which were produced and purified under identical conditions as described above in this example. Protein concentrations in the test samples were determined in microtiter plates by the method of Bradford (Bradford, 1976) according to Bio-Rad (Bio-Rad bulletin 1177 EG, 1984). Bovine serum albumin was used as standard. Enzyme activity was determined using the α-glucuronidase assay as described in Example 1. The specific activities were determined before and after deglycosylation using endoglycosidasee H (see Example 1). The results are shown in Table 13.3.

TABLE 13.3

Specific activity of recombinant α-glucuronidase

| | Specific activity glycosylated, μ/mg | Specific activity deglycosylated, μ/mg |
|---|---|---|
| Native | 22.0 | 32 |
| Recombinant | 21.7 | 26 |

It was found that deglycosylation of the enzymes resulted in an enhancement of the specific activities.

13.11. Determination of the Isoelectric Point (pI) for Recombinant α-glucuronidase Isoelectric focusing (IEF) was performed using a Phast System (Pharmacia). The fraction from the above purification containing the recombinant α-glucuronidase was desalted in 20 mM Na-acetate, pH 5.0 and separated on an IEF gel with a pH gradient of 4.0 to 6.5. Electrophoresis and silver staining conditions were as recommended by the manufacturer.

Isoelectric focusing pI markers (pI 2.5 to 6.5) from Pharmacia were used as pI standards.

The pI for the recombinant α-glucuronidase was determined to just below 5.2. This corresponds well with the pI obtained for the native α-glucuronidase.

EXAMPLE 14

Effect of Recombinant α-glucuronidase on Dough Properties and Bread Quality

This example illustrates how purified recombinant α-glucuronidase affects dough properties and bread quality either alone or in combination with xylanases having different substrate affinities with respect to water insoluble pentosans (WIP) and water soluble pentosans (WSP), respectively.

The enzymes were tested using a Danish roll recipe having the following composition (weight in g): wheat flour 1500, water 877.5, yeast 90, ascorbic acid 0.09, fungal α-amylase (16.2 units/g) 0.40 and salt 24.

A dough was prepared using the following method: The ingredients were kneaded using a Hobart 2 kneading machine for 2 min at low speed and 9 min at high speed. The temperature of the finished dough was 26° C. The first proofing of the dough covered by cloth was carried out at 30° C. After moulding to rolls using a moulder, a second proofing was carried out at 30° C. and 85% RH for 45 min. The proofed rolls were baked in a Miwe oven at 220° C. for 15 min.

A total of 7 batches of samples of doughs and the corresponding baked rolls were prepared:

sample 1 is the above basic recipe (control), sample 2 is basic dough containing 15 units of α-glucuronidase, sample 3 is basic dough containing 3600 GPU of a xylanase having high WIP activity, sample 4 is basic dough containing 15 units of α-glucuronidase and 3600 GPU of a xylanase having high WIP activity, sample 5 is basic dough containing 30 units of α-glucuronidase and 3600 GPU of a xylanase having high WIP activity, sample 6 is a basic dough containing 3600 GPU of a xylanase having a high WSP activity, and sample 7 is the basic dough containing 15 units of recombinant α-glucuronidase: and 3600 GPU of a xylanase having a high WSP activity.

The following tests were carried out:

Measurement of dough liquid viscosity. Was measured just before baking by the following procedure: 10 ml of distilled water was added to 5 g of dough followed by homogenisation for 1 min using an Ultra-Turrax T 25 (IKA). The dough suspension was centrifuged at 10600×g for 2 min. Viscosity measurements were conducted on the resulting supernatant at 10° C. and 20 rpm, using a Brookfield cone (cp40) and plate system.

Measurement of gluten index. Was performed essentially as described in the ICC method 155/AACC 38–12 except that the gluten was allowed to relax 10 min in a 2% salt solution before centrifugation. The gluten index was obtained by dividing the gluten remaining on the sieve after centrifugation with the total amount of gluten. Measurements were conducted on the dough just before baking.

Measurement of specific volume. The specific volume (ml/g) of the baked rolls was calculated by measuring the volume of 30 rolls by the rape seed displacement method and dividing it by the weight of the rolls.

Evaluation of crumb structure of baked rolls. Was carried out by visual evaluation according to the following scale: very poor 1, poor 2, non-uniform/medium 3, uniform/good 4, very good 5.

The results of the above tests are summarized in Table 14.1:

TABLE 14.1

The effect of recombinant α-glucuronidase alone and in combination with xylanases on dough properties and bread quality

| | GPU* | Units α-glucuro-nidase | Dough liquid visco-sity) (cP) | Specific volume (ml/g) | Crumb struc-ture | Gluten index |
|---|---|---|---|---|---|---|
| 1 | | | 4.1 | 5.98 | 4 | 86 |
| 2 | | 15 | 4.6 | 6.6 | 4 | 96 |
| 3 | 3600 | | 7.3 | 6.3 | 4 | 88 |
| 4 | 3600 | 15 | 7.9 | 6.8 | 4 | 95 |
| 5 | 3600 | 30 | 8.2 | 6.3 | 4 | 86 |
| 6 | 3600 | | 4.9 | 6.0 | 3 | 78 |
| 7 | 3600 | 15 | 5.7 | 5.8 | 3 | 74 |

*xylanase units measured according to the method described in Example 1.

It appears from the above table that the addition of 15 units of the recombinant α-glucuronidase alone has an improving effect on dough liquid viscosity, specific volume and gluten index.

The effect of a combination of the α-glucuronidase and a xylanase, in particular on dough liquid viscosity depends on the type of xylanase with which it is combined. The xylanase in samples 3, 4 and 5 (marked ^) has a preferential affinity for water insoluble pentosans (WIP) and its activity results in relatively high dough viscosity whereas the xylanase used in the above samples 6 and 7 has a high WSP activity and its activity results in a relatively low dough liquid viscosity.

The results indicate that when the hydrolysis products of the xylanase are relatively large fragments (high viscosity) as in samples 3, 4 and 5, aggregation of soluble arabinoxylan fragments occur after addition of α-glucuronidase, possibly as a consequence of cleavage of the charged glucuronic acid substituents. This assumption was affirmed by DIONEX analysis which showed a decrease of the content of arabinose and xylose in the dough liquid. This resulted in an increased gluten index and increased specific loaf volumes.

The same effect was not observed when using xylanase where the hydrolysisproducts are relatively small fragments (sample 7). Under these conditions an increased hydrolysis was observed when α-glucuronidase was added (measured by total amount of arabinose and xylose in the dough liquid) resulting in reduced gluten index and reduced specific volume.

However, based on these findings it is expected that the use of α-glucuronidase in combination with a xylanase producing small arabinoxylan fragments is of considerable interest in the production of dry baked products such as crackers and crispbread.

EXAMPLE 15

The Effect of Recombinant α-glucuronidase on Mineral Release in Animal Feed

The experiment was designed to study the effect of the recombinant α-glucuronidase on the release of metal ions from animal feed, either alone or in combination with a commercial enzyme product.

The enzyme preparations used were the purified recombinant α-glucuronidase as described in Example 13, having an enzymatic activity of 11 units/ml and the commercial product GRINDAZYM™ GP 5000 (Danisco Ingredients A/S) containing 18000 GPU/g.

For the experiment 40 g of milled chicken feed was washed with 150 ml of distilled water followed by centrifugation at 27000×g for 10 min. The washing procedure was repeated 8 times. 1 g of freeze-dried washed chicken feed was suspended in 8.6 ml of 20 mM Na-acetate buffer, pH 5.0, containing the enzymes to be tested. The suspensions were placed in dialysis tubes (Spectra/por 3, 3500 kDa having a diameter of 29 mm, length 100 mm). The dialysis tubes were submerged in acid washed beakers containing 200 ml of milli Q water. Samples of 5 ml were taken out from the beakers after 20 hours of dialysis and the content of metal ions was determined using flame ionization spectrometry. The results (average of duplicate samples) are summarized in Table 15.1.

TABLE 15.1

Effect of α-glucuronidase on release of metal ions in chicken feed

| | ppm Na | ppm K | ppm Ca | ppm Mg |
|---|---|---|---|---|
| Control | 49.5 | 7.1 | 13 | 3.5 |
| α-glucuronidase, 2 units/g | 52.0 | 7.6 | 13 | 3.5 |
| GP 5000, 9 GPU/g | 51.0 | 7.3 | 13 | 3.5 |
| α-glucuronidase, 2 units/g + GP 5000, 9 GPU/g | 57.0 | 8.5 | 14 | 3.9 |

The results show that α-glucuronidase has an effect on release of metal ions to a dialysable form. The effect is particularly evident for the release of K, Na and Mg ions in combination with the xylanase product GP 5000. With respect to release of K and Na ions there appears to be a synergistic effect of the two enzyme preparations.

REFERENCES

Bio-Rad Bulletin 1177 EG (1984) Automated protein assay.
Bradford, M. M. (1976) A rapid and sensitive method for the quantitation of microgram quantities of protein utilizing the principle of protein-dye binding. Anal. Biochem. 72, 248–254.
Buchert, J., Siika-aho, M., Rättö, M., Viikari, L. and Bailey, M. (1993) Method and enzymatic preparation for the treatment of cellulose pulps. International patent application, WO 93/11296.
Bussink, H. J. D.; Buxton, F. P.; Visser, J.; Current Genetics 19:467–474 (1991).
Christov, L. P. and Prior, B. A. (1993) Xylan removal from dissolving pulp using enzymes of *Aureobasidium pullulans*. Biotechnology Letters, 15, 1269–1274.
Dusterhöft, E.-M. (1993) Characterisation and enzymic degradation of non-starch polysaccharides in lignocellulosic by-products. PhD thesis, Wageningen Agricultural University, pp 2–3.
Harinsen, J. A. M.; Kusters-van Someren, M. A.; Visser, J.; Current Genetics 18:161–166 (1990)
Idouraine, A., Hassani, B. Z., Claye, S. S. and Weber, C. W. (1995) In vitro binding capacity of various fiber sources for magnesium, zinc, and copper. J. Agric. Food Chem. 43, 1580–1584.
Ishihara, M., Inagaki, S., Hayashi, N. and Shimizu, K. (1990) 4-O-methyl-D-glucuronic acid residue liberating enzyme in the enzymatic hydrolysis of hardwood xylan. Bull. For. & For. Prod. Res. Inst. 359, 141–157.
Kawabata, Y., Ono, K., Gama, Y., Yoshida, S., Kobayashi, H. and Kusakabe, I. (1995) Purification and characterization of α-glucuronidase from snail acetone powder. Biosci. Biotech. Biochem. 59, 1086–1090.
Khandke, K. M., Vithayathil, P. J. and Murthy, S. K. (1989) Purification and characterization of an alfa-D-glucuronidase from a thermophilic fungus, *Thermoascus aurantiacus*. Arch. Biochem. Biophys. 274, 511–517.
Korte, H. E. (1990) Reinigung und Charakterisierung einer alfa-glucuronidase aus *Agaricus bisporus* (Lge.) Sing. und Untersuchungen an substituierten Xylooligomeren. PhD thesis, University of Hamburg.
Milner, Y. and Avigad, G. (1967) A copper reagent for the determination of hexuronic acids and certain ketohexoses. Carbohyd. Res. 4, 359–361.
Nelson, N. (1944) A photometric adaptation of the Somogyi method for the determination of glucose. J. Biol. Chem. 153, 375–380.
Odier, E. and Artaud, I. (1992) Degradation of lignin in Microbial Degradation of Natural Products (Winkelmann, G. ed.), pp 161–191.
Olsen, W. L., Gallagher, H. P., Burris, K. A., Bhattacharjee, S. S., Slocomb, J. P. and DeWitt, D. M.,(1990) Enzymatic delignification of lignocellulosic material. International patent application, EP 0 406 617 A2.
Perrella, F. W. (1988) EZ-FIT: A practical curve-fitting microcomputer program for the analysis of enzyme kinetic data on IBM-PC compatible computers. Anal. Biochem. 174, 437–447.
Puls, J. and Schuseil, J. (1993) Chemistry of hemicelluloses: relationship between hemicellulose structure and enzymes required for hydrolysis. In Hemicellulose and hemicellulases (Coughlan, M. P. and Hazlewood, G. P., eds.), pp 1–27. University Press, Cambridge.
Roberts, J. C., McCarthy, A. J., Flynn, N. J. and Broda, P. (1990) Modification of paper properties by the pretreatment of pulp with *Saccharomonospora viridis* xylanase. Enzyme Microb. Technol. 12, 210–213.
Shao, W., Obi, S. K. C., Puls, J. and Wiegel, J. (1995) Purification and characterization of the alfa-glucuronidase from *Thermoanaerobacterium* sp. strain JW/SL-YS485, an important enzyme for the utilization of substituted xylans. Appl. Environ. Microbiol. 61, 1077–1081.
Siika-aho, M., Tenkanen, M., Buchert, J., Puls, J. and Viikari, L. (1994) An α-glucuronidase from *Trichoderma reesei* RUT C-30. Enzyme Micrbb. Technol. 16, 813–819.
Timell, T. E. (1967) Recent progress in the chemistry of wood hemicelluloses. Wood Sci. Technol. 1, 45–70.
Uchida, H., Kusakabe, I., Kawabata, Y., Ono, T. and Murakami, K. (1992a) Production. of xylose from xylan with intracellular enzyme system of *Aspergillus niger* 5-16. J. Ferment. Bioeng. 74, 153–158.
Uchida, H., Nanri, T., Kawabata, Y., Kusakabe, I and Murakami, K. (1992b) Purification and characterization of intracellular alfa-glucuronidase from *Aspergillus niger* 5-16. Biosci. Biotech. Biochem. 56,1608–1615.
Viikari, L. (1994) Use of biotechnology in the pulp and paper industry. Comett course 30.5.–1.6. 1994, Finland.
Viikari, L., Kantelinen, A., Sundquist, J. and Linko, M. (1994) Xylanases in bleaching: from an idea to the industry. FEMS Microbiology Reviews, 13, 335–350.
Viikari, L., Tenkanen, M., Buchert, J., Rättö, M., Bailey, M., Siika-aho, M. and Linko, M. (1993) Hemicellulases for industrial applications. In Bioconversion of fresh and agricultural plant residues (Saddler, N., ed.), pp 131–182.
Voragen, A. G. J., Gruppen, H., Verbruggen, M. A. and Vietor, R. J. (1992) Characterization of cereal arabinoxylans. In Xylans and xylanases (Visser, J. et al. ed.) pp 51–67. Elsevier, Amsterdam.
Welt, T. and Dinus, R. J. (1995) Enzymatic deinking—a review. Progress in Paper Recycling, February, 36–47.

What is claimed is:

1. A method of enhancing the volume of a baked product made from a dough by at least 5%, the method comprising adding to the dough an effective amount of an alpha-glucuronidase that comprises at least one of:
- an alpha-glucuronidase naturally produced by an organism selected from the group consisting of *Trichoderma reseei, Trichoderma viride,* Aspergillus spp., *Thermoascus aurantiacus, Agaricus bisporus* and a Thermoanaerobacter sp, said alpha-glucuronidase exhibiting enzymatic activity at a pH in the range of 4 to 6.67 and having a molecular weight above 90 kDa.;
- an alpha-glucuronidase expressed by the phage lambda NCIMB 40801 and encoded by the coding sequence as shown in SEQ ID NO: 22; or
- an alpha-glucuronidase encoded by a DNA sequence that hybridizes to the coding sequence as shown in SEQ ID NO: 22 under the following conditions:
  pre-hybridization for 3 hours, hybridization under Southern blotting conditions at 65° C. and washing 2×20 minutes in 2×SSC, 0.5% SDS followed by 2×20 minutes in 0.2 SSC, 0.5% SDS,
  wherein the enhancement of the volume of the baked product made from a dough can be obtained without the addition of a further enzyme.

2. A method according to claim 1 wherein the α-glucuronidase is an enzyme comprising at least one of the amino acid sequences:
   (i) EDGYDGWLRYAPVHRDLH (SEQ ID NO:1);
   (ii) XDGYDGWLRYAPVSCDLHCRQALPSHIV-LLXSTK (SEQ ID NO: 2);
   (iii) AGFQSILSTXLTSHPFQXDSSASIL-VATLDXYRQK (SEQ ID NO: 3);
   (iv) IXGEADGVEPAPVDYVV (SEQ ID NO:4);
   (v) APSGVYDIGVNYYDLYGGQSK (SEQ ID NO:5);
   (vi) YGPIDFQVREPTSPLFANLYQT-NTAIELEVSQEYLGQQCH (SEQ ID NO: 6);
   (vii) WTLSVGDK (SEQ ID NO: 7); and
   (viii) TVLDFDLRVDHKPSMVRDIISGQR-FXRTLGGWAAVVNVGTXR (SEQ ID NO: 8)
   where X can be any amino acid.

3. A method according to claim 1 wherein there is added at least one further enzyme to the dough.

4. A method according to claim 1 wherein the volume is increased by at least 5% as determined by the rape seed displacement method.

5. A method according to claim 1 wherein the volume is increased by at least 10%, as determined by the rape seed displacement method.

6. A method according to claim 1 wherein the amount of α-glucuronidase being added is within the range of 1–100 units per kg flour.

7. A method according to claim 3 wherein the at least one further enzyme is a xylanase.

8. A method according to claim 1 wherein the alpha-glucuronidase is coded for by an isolated DNA fragment obtainable from an Aspergillus species, the fragment comprising at least one of:
   (a) a fragment coding for an enzyme comprising at least one of the amino acid sequences:
      (i) EDGYDGWLRYAPVHRDLH (SEQ ID NO:1);
      (ii) XDGYDGWLRYAPVSCDLHCRQALPSHIV-LLXSTK (SEQ ID NO:2);
      (iii) AGFQSILSTXLTSHPFQXDSSASIL-VATLDXYRQK (SEQ ID NO:3);
      (iv) IXGEADGVEPAPVDYVV (SEQ ID NO:4);
      (v) APSGVYDIGVNYYDLYGGQSK (SEQ ID NO:5);
      (vi) YGPIDFQVREPTSPLFANLYQT-NTAIELEVSQEYLGQQCH (SEQ ID NO:6);
      (vii) WTLSVGDK (SEQ ID NO:7);
      (viii) TVLDFDLRVDHKPSMVRDIISGQR-FXRTLGGWAAVVNVGTXR (SEQ ID NO:8); or
      (ix) EDGYNGWLRYAPVSXDLHXRQALPSHIVLL (SEQ ID NO: 20), where X can be any amino acid; or
   (b) a DNA fragment coding for alpha-glucuronidase as comprised in the pg lambda deposited under the accession number NCIMB 40801.

9. A method according to claim 1 wherein the α-glucuronidase is produced by a heterologous species.

10. A method according to claim 1 wherein the alpha-glucuronidase is glycosylated.

11. A method according to claim 1 wherein the alpha-glucuronidase is non-glycosylated.

12. A method according to claim 1 wherein the alpha-glucuronidase is produced by cultivating a host cell which is transformed with a recombinant vector into which a DNA fragment comprising a sequence coding for said alpha-glucuronidase is inserted, under conditions where said alpha-glucuronidase is expressed, and harvesting the enzyme from the cell and/or the cultivation medium.

13. A method according to claim 12 wherein the inserted DNA fragment is obtainable from an Aspergillus species, the fragment comprising at least one of:

a) a fragment coding for an enzyme comprising at least one of the amino acid sequences:
(i) EDGYDGWLRYAPVHRDLH (SEQ ID NO:1);
(ii) XDGYDGWLRYAPVSCDLHCRQALPSHIV-LLXSTK (SEQ ID NO:2);
(iii) AGFQSILSTXLTSHPFQXDSSASIL-VATLDXYRQK (SEQ ID NO;3);
(iv) IXGEADGVEPAPVDYVV (SEQ ID NO:4);
(v) APSGVYDIGVNYYDLYGGQSK (SEQ ID NO:5);
(vi) YGPIDFQVREPTSPLFANLYQT-NTAIELEVSQEYLGQQCH (SEQ ID NO:6);
(vii) WTLSVGDK (SEQ ID NO:7);
(viii) TVLDFDLRVDHKPSMVRDIISGQR-FXRTLGGWAAVVNVGTXR (SEQ ID NO:8); or
(ix) EDGYNGWLRYAPVSXDLHXRQALPSHIVLL (SEQ ID NO:20),
where X can be any amino acid; or
(b) a DNA fragment coding for α-glucuronidase as comprised in the phage lambda deposited under the accession number NCIMB 40801.

14. A method according to claim 12 wherein the recombinant vector comprises the construct pIM3212.

15. A method according to claim 12 wherein the host cell is selected from a fungal species, a bacterial species, a plant cell and an animal cell.

16. A method according to claim 15 wherein the host cell is derived from a fungal species selected from the group consisting of a yeast species, a Trichoderma species, an Aspergillus species, a Thermoascus species, an Agaricus species and a Thermoanaerobacterium species.

17. A method according to claim 1 wherein the alpha-glucuronidase comprises at least one of:
an alpha-glucuronidase naturally produced by an organism selected from the group consisting of *Trichoderma reseei, Trichoderma viride,* Aspergillus spp., *Thermoascus aurantiacus, Agaricus bisporus* and a Thermoanaerobacter sp. or an alpha-glucuronidase expressed by the phage lambda NCIMB 40801 and encoded by the coding sequence as shown in SEQ ID No: 22.

18. A method of improving the nutritional value of an animal feed component, the method comprising adding to the feed component a preparation comprising alpha-glucuronidase at an amount that, in the presence of enzymes of an animal digestive tract and in the absence of other enzymes, results in a reduction in residual dry matter of the feed component of at least 10%, wherein the alpha-glucuronidase comprises at least one of:
an alpha-glucuronidase naturally produced by an organism selected from the group consisting of *Trichoderma reseei, Trichoderma viride,* Aspergillus spp., Thermoascus aurantiacus, Agaricus bisporus and a Thermoanaerobacter sp., said alpha-glucuronidase exhibiting enzymatic activity at a pH in the range of 4 to 6.67 and having molecular weight above 90 kDa;
an alpha-glucuronidase expressed by the phage lambda NCIMB 40801 and encoded by the coding sequence as shown in SEQ ID NO: 22; or
an alpha-glucuronidase encoded by a DNA sequence that hybridizes to the coding sequence as shown in SEQ ID NO: 22 under the following conditions:
pre-hybridization for 3 hours, hybridization under Southern blotting conditions at 65° C. and washing 2×20 minutes in 2×SSC, 0.5% SDS followed by 2×20 minutes in 0.2 SSC, 0.5% SDS.

19. A method according to claim 18, wherein the preparation containing alpha-glucuronidase does not contain other enzymes.

20. A method according to claim 18, wherein a hemicellulose degrading enzyme is added to the feed component.

21. A method according to claim 18, wherein the addition of the preparation comprising alpha-glucuronidase results in a reduction in residual dry matter of the feed component of at least 15%.

22. A method according to claim 18, wherein the addition of the preparation comprising alpha-glucuronidase, in addition to resulting in a reduction in residual dry matter of the feed component of at least 10%, results in an increase of the amount of dialyzable metal ions in the feed component of at least 5%.

23. A method according to claim 18, wherein the alpha-glucuronidase is an enzyme naturally produced by an organism selected from the group consisting of *Trichoderma reseel, Trichoderma viride,* Aspergillus spp., *Thermoascus aurantiacus, Agaricus bisporus* and a Thermoanaerobacter sp.

24. A method according to claim 1 or 17 wherein the Aspergillus spp. is *Aspergillus niger* or *Aspergillus tubigensis*.

25. A method according to claim 18 or 23 wherein the Aspergillus spp. is *Aspergillus niger* or *Aspergillus tubigensis*.

26. A method according to claim 1 wherein the alpha-glucuronidase encoded by a DNA sequence that hybridizes to the coding sequence as shown in SEQ ID NO: 22 comprises at least one amino acid sequence selected from the group consisting of:
(i) EDGYDGWLRYAPVHRDLH (SEQ ID NO:1);
(ii) XDGYDGWLRYAPVSCDLHCRQALPSHIV-LLXSTK (SEQ ID NO:2);
(iii) AGFQSILSTXLTSHPFQXDSSASIL-VATLDXYRQK (SEQ ID NO:3);
(iv) IXGEADGVEPAPVDYVV (SEQ ID NO:4);
(v) APSGVYDIGVNYYDLYGGQSK (SEQ ID NO: 5);
(vi) YGPIDFQVREPTSPLFANLYQT-NTAIELEVSQEYLGQQCH (SEQ ID NO:6);
(vii) WTLSVGDK (SEQ ID NO:7);
(viii) TVLDFDLRVDHKPSMVRDIISGQR-FXRTLGGWAAVVNVGTXR (SEQ ID NO:8); and
(ix) EDGYNGWLRYAPVSXDLHXRQALPSHIVLL (SEQ ID NO: 20),
where X can be any amino acid.

27. A method according to claim 18, wherein the alpha-glucuronidase encoded by a DNA sequence that hybridizes to the coding sequence as shown in SEQ ID NO: 22 comprises at least one amino acid sequence selected from the group consisting of:
(i) EDGYDGWLRYAPVHRDLH (SEQ ID NO:1);
(ii) XDGYDGWLRYAPVSCDLHCRQALPSHIV-LLXSTK (SEQ ID NO:2);
(iii) AGFQSILSTXLTSHPFQXDSSASIL-VATLDXYRQK (SEQ ID NO:3);
(iv) IXGEADGVEPAPVDYVV (SEQ ID NO:4);
(v) APSGVYDIGVNYYDLYGGQSK (SEQ ID NO: 5);
(vi) YGPIDFQVREPTSPLFANLYQT-NTAIELEVSQEYLGQQCH (SEQ ID NO:6);
(vii) WTLSVGDK (SEQ ID NO:7);
(viii) TVLDFDLRVDHKPSMVRDIISGQR-FXRTLGGWAAVVNVGTXR (SEQ ID NO:8); and
(ix) EDGYNGWLRYAPVSXDLHXRQALPSHIVLL (SEQ ID NO: 20),
where X can be any amino acid.

* * * * *

SEQUENCE LISTING

<160> NUMBER OF SEQ ID NOS: 22

<210> SEQ ID NO 1
<211> LENGTH: 18
<212> TYPE: PRT
<213> ORGANISM: Unknown
<220> FEATURE:
<223> OTHER INFORMATION: Aspergillus Alpha-Glucuronidase Peptide

<400> SEQUENCE: 1

Glu Asp Gly Tyr Asp Gly Trp Leu Arg Tyr Ala Pro Val His Arg Asp
1               5                   10                  15

Leu His

<210> SEQ ID NO 2
<211> LENGTH: 34
<212> TYPE: PRT
<213> ORGANISM: Unknown
<220> FEATURE:
<223> OTHER INFORMATION: Aspergillus Alpha-Glucuronidase Peptide
<221> NAME/KEY: MISC_FEATURE
<222> LOCATION: (1)..(1)
<223> OTHER INFORMATION: Xaa equals any of the naturally occurring
      L-amino acids
<221> NAME/KEY: MISC_FEATURE
<222> LOCATION: (31)..(31)
<223> OTHER INFORMATION: Xaa equals any of the naturally occurring
      L-amino acids

<400> SEQUENCE: 2

Xaa Asp Gly Tyr Asp Gly Trp Leu Arg Tyr Ala Pro Val Ser Cys Asp
1               5                   10                  15

Leu His Cys Arg Gln Ala Leu Pro Ser His Ile Val Leu Leu Xaa Ser
            20                  25                  30

Thr Lys

<210> SEQ ID NO 3
<211> LENGTH: 35
<212> TYPE: PRT
<213> ORGANISM: Unknown
<220> FEATURE:
<223> OTHER INFORMATION: Aspergillus Alpha-Glucuronidase Peptide
<221> NAME/KEY: MISC_FEATURE
<222> LOCATION: (10)..(10)
<223> OTHER INFORMATION: Xaa equals any of the naturally occurring
      L-amino acids
<221> NAME/KEY: MISC_FEATURE
<222> LOCATION: (18)..(18)
<223> OTHER INFORMATION: Xaa equals any of the naturally occurring
      L-amino acids
<221> NAME/KEY: MISC_FEATURE
<222> LOCATION: (31)..(31)
<223> OTHER INFORMATION: Xaa equals any of the naturally occurring
      L-amino acids

<400> SEQUENCE: 3

Ala Gly Phe Gln Ser Ile Leu Ser Thr Xaa Leu Thr Ser His Pro Phe
1               5                   10                  15

Gln Xaa Asp Ser Ser Ala Ser Ile Leu Val Ala Thr Leu Asp Xaa Tyr
            20                  25                  30

Arg Gln Lys
        35

<210> SEQ ID NO 4
<211> LENGTH: 17

```
<212> TYPE: PRT
<213> ORGANISM: Unknown
<220> FEATURE:
<223> OTHER INFORMATION: Aspergillus Alpha-Glucuronidase Peptide
<221> NAME/KEY: MISC_FEATURE
<222> LOCATION: (2)..(2)
<223> OTHER INFORMATION: Xaa equals any of the naturally occurring
      L-amino acids

<400> SEQUENCE: 4

Ile Xaa Gly Glu Ala Asp Gly Val Glu Pro Ala Pro Val Asp Tyr Val
1               5                   10                  15

Val

<210> SEQ ID NO 5
<211> LENGTH: 21
<212> TYPE: PRT
<213> ORGANISM: Unknown
<220> FEATURE:
<223> OTHER INFORMATION: Aspergillus Alpha-Glucuronidase Peptide

<400> SEQUENCE: 5

Ala Pro Ser Gly Val Tyr Asp Ile Gly Val Asn Tyr Tyr Asp Leu Tyr
1               5                   10                  15

Gly Gly Gln Ser Lys
            20

<210> SEQ ID NO 6
<211> LENGTH: 40
<212> TYPE: PRT
<213> ORGANISM: Unknown
<220> FEATURE:
<223> OTHER INFORMATION: Aspergillus Alpha-Glucuronidase Peptide

<400> SEQUENCE: 6

Tyr Gly Pro Ile Asp Phe Gln Val Arg Glu Pro Thr Ser Pro Leu Phe
1               5                   10                  15

Ala Asn Leu Tyr Gln Thr Asn Thr Ala Ile Glu Leu Glu Val Ser Gln
            20                  25                  30

Glu Tyr Leu Gly Gln Gln Cys His
        35                  40

<210> SEQ ID NO 7
<211> LENGTH: 8
<212> TYPE: PRT
<213> ORGANISM: Unknown
<220> FEATURE:
<223> OTHER INFORMATION: Aspergillus Alpha-Glucuronidase Peptide

<400> SEQUENCE: 7

Trp Thr Leu Ser Val Gly Asp Lys
1               5

<210> SEQ ID NO 8
<211> LENGTH: 42
<212> TYPE: PRT
<213> ORGANISM: Unknown
<220> FEATURE:
<223> OTHER INFORMATION: Aspergillus Alpha-Glucuronidase Peptide
<221> NAME/KEY: MISC_FEATURE
<222> LOCATION: (26)..(26)
<223> OTHER INFORMATION: Xaa equals any of the naturally occurring
      L-amino acids
<221> NAME/KEY: MISC_FEATURE
<222> LOCATION: (41)..(41)
<223> OTHER INFORMATION: Xaa equals any of the naturally occurring
      L-amino acids
```

<400> SEQUENCE: 8

Thr Val Leu Asp Phe Asp Leu Arg Val Asp His Lys Pro Ser Met Val
1               5                   10                  15

Arg Asp Ile Ile Ser Gly Gln Arg Phe Xaa Arg Thr Leu Gly Gly Trp
                20                  25                  30

Ala Ala Val Val Asn Val Gly Thr Xaa Arg
            35                  40

<210> SEQ ID NO 9
<211> LENGTH: 34
<212> TYPE: PRT
<213> ORGANISM: Unknown
<220> FEATURE:
<223> OTHER INFORMATION: Aspergillus Alpha-Glucuronidase Peptide
<221> NAME/KEY: MISC_FEATURE
<222> LOCATION: (1)..(1)
<223> OTHER INFORMATION: Xaa is Cys or Glu
<221> NAME/KEY: MISC_FEATURE
<222> LOCATION: (31)..(31)
<223> OTHER INFORMATION: Xaa equals any of the naturally occurring
      L-amino acids

<400> SEQUENCE: 9

Xaa Asp Gly Tyr Asp Gly Trp Leu Arg Tyr Ala Pro Val Ser Cys Asp
1               5                   10                  15

Leu His Cys Arg Gln Ala Leu Pro Ser His Ile Val Leu Leu Xaa Ser
                20                  25                  30

Thr Lys

<210> SEQ ID NO 10
<211> LENGTH: 35
<212> TYPE: PRT
<213> ORGANISM: Unknown
<220> FEATURE:
<223> OTHER INFORMATION: Aspergillus Alpha-Glucuronidase Peptide
<221> NAME/KEY: MISC_FEATURE
<222> LOCATION: (10)..(10)
<223> OTHER INFORMATION: Xaa equals any of the naturally occurring
      L-amino acids
<221> NAME/KEY: MISC_FEATURE
<222> LOCATION: (18)..(18)
<223> OTHER INFORMATION: Xaa is Cys or Glu but uncertain
<221> NAME/KEY: MISC_FEATURE
<222> LOCATION: (31)..(31)
<223> OTHER INFORMATION: Xaa is Glu but uncertain

<400> SEQUENCE: 10

Ala Gly Phe Gln Ser Ile Leu Ser Thr Xaa Leu Thr Ser His Pro Phe
1               5                   10                  15

Gln Xaa Asp Ser Ser Ala Ser Ile Leu Val Ala Thr Leu Asp Xaa Tyr
                20                  25                  30

Arg Gln Lys
        35

<210> SEQ ID NO 11
<211> LENGTH: 23
<212> TYPE: PRT
<213> ORGANISM: Unknown
<220> FEATURE:
<223> OTHER INFORMATION: Aspergillus Alpha-Glucuronidase Peptide
<221> NAME/KEY: MISC_FEATURE
<222> LOCATION: (2)..(2)
<223> OTHER INFORMATION: Xaa is Ile or Lys
<221> NAME/KEY: CARBOHYD
<222> LOCATION: (6)..(6)
<223> OTHER INFORMATION: Potential Glycosylation Site

```
<221> NAME/KEY: CARBOHYD
<222> LOCATION: (18)..(18)
<223> OTHER INFORMATION: Potential Glycosylation Site

<400> SEQUENCE: 11

Ile Xaa Gly Glu Ala Asp Gly Val Glu Pro Ala Pro Val Asp Tyr Val
1               5                   10                  15

Val Leu Leu Pro Lys Gly Lys
            20

<210> SEQ ID NO 12
<211> LENGTH: 20
<212> TYPE: DNA
<213> ORGANISM: Artificial Sequence
<220> FEATURE:
<223> OTHER INFORMATION: agu-5 nucleotide

<400> SEQUENCE: 12
ggaccaatag acttccaagt                                           20

<210> SEQ ID NO 13
<211> LENGTH: 20
<212> TYPE: DNA
<213> ORGANISM: Artificial Sequence
<220> FEATURE:
<223> OTHER INFORMATION: agu-5 nucleotide

<400> SEQUENCE: 13
ggccccatcg attttcaggt                                           20

<210> SEQ ID NO 14
<211> LENGTH: 20
<212> TYPE: DNA
<213> ORGANISM: Artificial Sequence
<220> FEATURE:
<223> OTHER INFORMATION: agu-5 nucleotide

<400> SEQUENCE: 14
gggccgattg acttccaagt                                           20

<210> SEQ ID NO 15
<211> LENGTH: 20
<212> TYPE: DNA
<213> ORGANISM: Artificial Sequence
<220> FEATURE:
<223> OTHER INFORMATION: agu-5 nucleotide

<400> SEQUENCE: 15
ggtcctatag acttccaagt                                           20

<210> SEQ ID NO 16
<211> LENGTH: 20
<212> TYPE: DNA
<213> ORGANISM: Artificial Sequence
<220> FEATURE:
<223> OTHER INFORMATION: agu-9 nucleotide

<400> SEQUENCE: 16
aaatcataat aattaacacc                                           20

<210> SEQ ID NO 17
<211> LENGTH: 20
<212> TYPE: DNA
<213> ORGANISM: Artificial Sequence
<220> FEATURE:
<223> OTHER INFORMATION: agu-9 nucleotide
```

<400> SEQUENCE: 17
aggtcgtagt agttcacccc                                               20

<210> SEQ ID NO 18
<211> LENGTH: 20
<212> TYPE: DNA
<213> ORGANISM: Artificial Sequence
<220> FEATURE:
<223> OTHER INFORMATION: agu-9 nucleotide

<400> SEQUENCE: 18
aaatcataat aattgacgcc                                               20

<210> SEQ ID NO 19
<211> LENGTH: 20
<212> TYPE: DNA
<213> ORGANISM: Artificial Sequence
<220> FEATURE:
<223> OTHER INFORMATION: agu-9 nucleotide

<400> SEQUENCE: 19
aaatcataat aatttactcc                                               20

<210> SEQ ID NO 20
<211> LENGTH: 30
<212> TYPE: PRT
<213> ORGANISM: Unknown
<220> FEATURE:
<223> OTHER INFORMATION: Aspergillus Alpha-Glucuronidase Peptide
<221> NAME/KEY: MISC_FEATURE
<222> LOCATION: (15)..(15)
<223> OTHER INFORMATION: Xaa is probably Cys but uncertain
<221> NAME/KEY: MISC_FEATURE
<222> LOCATION: (19)..(19)
<223> OTHER INFORMATION: Xaa is probably Cys but uncertain

<400> SEQUENCE: 20

Glu Asp Gly Tyr Asn Gly Trp Leu Arg Tyr Ala Pro Val Ser Xaa Asp
1               5                   10                  15

Leu His Xaa Arg Gln Ala Leu Pro Ser His Ile Val Leu Leu
            20                  25                  30

<210> SEQ ID NO 21
<211> LENGTH: 30
<212> TYPE: PRT
<213> ORGANISM: Unknown
<220> FEATURE:
<223> OTHER INFORMATION: Aspergillus Alpha-Glucuronidase Peptide
<221> NAME/KEY: MISC_FEATURE
<222> LOCATION: (15)..(15)
<223> OTHER INFORMATION: Xaa is probably Cys but uncertain
<221> NAME/KEY: MISC_FEATURE
<222> LOCATION: (19)..(19)
<223> OTHER INFORMATION: Xaa is probably Cys but uncertain

<400> SEQUENCE: 21

Glu Asp Gly Tyr Asp Gly Trp Leu Arg Tyr Ala Pro Val Ser Xaa Asp
1               5                   10                  15

Leu His Xaa Arg Gln Ala Leu Pro Ser His Ile Val Leu Leu
            20                  25                  30

<210> SEQ ID NO 22
<211> LENGTH: 2728
<212> TYPE: DNA
<213> ORGANISM: Aspergillus tubingensis

<400> SEQUENCE: 22

```
aatgcgggga gatcctgcaa acaggccatg acgtgtgtat atatgatgaa gaagagggct      60
ggtactccat agttctttgc gatggcatag ctggaaagaa acggccacta tgagaggttc     120
aaatctcttt caattgaccc tggctctttt actgtccttg gtagcagccg aggatgggta     180
caatggttgg ctccgatatg ctcccgtgtc ctgcgatctg cattgtcgac aggctttgcc     240
gtctcatatt gtgttgttga acagcaccaa aggaagcccg atcgagactg caggacgaga     300
attgaaagca ggattccaat cgattctttc gacgaactta acatttcatc catttcaatg     360
cgatagctcc gcatcaattc tggtggctac cctggatgag tatcgccaaa atgccggga     420
catcaacttg cccgagcttg atcccgatgg cttctggtta caatccgaag gggacacagt     480
tcgcatctta ggcaacaatg ccagaggagc cttgtacgga gcatacgaat acctcgctat     540
ggtggcacaa cgaaacttct ctcgtgtcgc gtacaccacc aacccacatg cgccgatccg     600
ttgggtaaat caatgggaca acatggacgg aagtattgaa cgaggctacg gtggcgcgtc     660
catattcttc aaagatggca cggtggtgga agacatggct cctgttgagc aatatgctag     720
gctgctcgca tctatacgga taaacgcaat tgtcgttaat aatgtcaatg cgaacgcaac     780
actactgcta cccgaaaata tgaaaggcct gggtcgcata gcagatgcct gtcgaccata     840
cggcgttcaa attggcatat cgctgaactt tgcttcacca gaaagcttgg gcggcctaga     900
aacttatgat ccacttgatc ctggtgtcat tgcatggtgg cagaatatca ccgatagcct     960
ctataccat gtaccagaca tggctgggta cctcgtcaaa gcagactcgg agggccagcc    1020
aggtccagat acatataatc gcacactctc acaaggggcg aatcttttcg cccgtgccct    1080
gcatccacat ggggggtgtgc ttatgtaccg cgccttcgtc tacaacgaca acttgaacga    1140
atcggactgg aaggctgatc gtgccaaggc agcagtggaa tacttcaagg acctggacgg    1200
tcagttctac gagaacgtcg tggtacagat aaagtacggc ccaatcgact ttcaagtacg    1260
cgagcctacc tcaccccttt tcgccaacct ctaccaaacc aacacagcca tagagttgga    1320
ggttagtcag gagtacctgg ggcagcaatg tcatttggtg tacctacctc cgctctggaa    1380
gacggtcctg gattttgact acgcgtaga tcacaagcct tcgatggtcc gcgatataat    1440
atccggacag cgcttcaaca gaacgctcgg gggctgggca gctgttgtta atgtgggcac    1500
taacagaaca tggctgggta gccaccttgc tatgtccaat ctgtacgctt atggtcgttt    1560
ggcctggagt ccgacagacg attctgaaca gatcctcaaa gactggactc gcctcacatt    1620
tggacaaaat cggcaagtca tcgacactat tgctgatatg cccatgacct cctggcctgc    1680
ctatgaaaac tatacaggca acctgggcat acagaccctg acagatatct tgtatactca    1740
ctatggccca aacccagcta cacaggataa caatggctgg ggtcaatgga cacgtgctga    1800
tcacaattca gttggaatgg accgaacaat atcgaatggc actgggtata ccggccaata    1860
tccggaggag gttgctcgct tatacgagtc actagaaact acgccagatg atctcgtctt    1920
gtggtttcac catgtaccat ggactcatcg tttgcattcc gggttgacag ttattcagca    1980
tttctacaac gctcactatg ctggctcaga agctgcacac ggctttataa gacaatggga    2040
gtctttaaaa ggactaattg atcgggagcg atacgaggcc atgcggtcac gccttgtcta    2100
ccaggcggga cactccattg tctggcgcga tgctatcaac aatttctact acaacatgac    2160
cggaattcca gatgtggctg gccgtgtggg tcatcatccg tggcgcattg aagctgagag    2220
tatgagattg gacggatacc agacgtacac tgtcagtccg ttcgaggccg cttctaacac    2280
tacggcaatt attaccacct ctaattcaac gactgggaca gcaagaacta ccatcaaagc    2340
```

```
cccttcggga gtatatgata taggggtgaa ctactacgat ctctatggcg gtcaatccaa    2400
gtggacatta tctgtgggtg acaaggtagt gggtcaatgg cttggggata tggagcatca    2460
atccctaggc catacaccgt ctatatactt ggacggtcac tcggccaccc ggataacgtt    2520
tcatggggtc gtcgtccggc agggtgatca gctgaaaatt gttggcgagg cgaatggggt    2580
cgagcctgct ccagtggatt atgtagtgct gctaccgcca ggggtggttg actgatatct    2640
acaaggtcct atgcgctatg taattgccga atatatatgc agatgaaact tttagtggcg    2700
ttctatatca ttggcgttcc agacaaga                                      2728
```